(12) United States Patent
Lambert et al.

(10) Patent No.: US 11,768,181 B2
(45) Date of Patent: *Sep. 26, 2023

(54) METHOD AND SYSTEM FOR ULTRASONIC CHARACTERIZATION OF A MEDIUM

(71) Applicants: SUPERSONIC IMAGINE, Aix-en-Provence (FR); CENTRE NATIONAL DE LA RECHERCHE SCIENTIFIQUE—CNRS, Paris (FR); Ecole Supérieure de Physique et de Chimie Industrielles de la Ville de Paris, Paris (FR)

(72) Inventors: William Lambert, Ivry sur Seine (FR); Alexandre Aubry, Ivry sur Seine (FR); Mathias Fink, Meudon (FR); Thomas Frappart, Aix en Provence (FR)

(73) Assignees: SUPERSONIC IMAGINE, Aix-en-Provence (FR); CENTRE NATIONAL DE LA RECHERCHE SCIENTIFIQUE—CNRS, Paris (FR); Ecole Supérieure de Physique et de Chimie Industrielles de la Ville de Paris, Paris (FR)

(*) Notice: Subject to any disclaimer, the term of this patent is extended or adjusted under 35 U.S.C. 154(b) by 68 days.

This patent is subject to a terminal disclaimer.

(21) Appl. No.: 17/473,080

(22) Filed: Sep. 13, 2021

(65) Prior Publication Data

US 2022/0082529 A1 Mar. 17, 2022

(30) Foreign Application Priority Data

Sep. 15, 2020 (FR) .................................... 20 09314

(51) Int. Cl.
*G01N 29/07* (2006.01)
*G01N 29/04* (2006.01)
*A61B 8/15* (2006.01)

(52) U.S. Cl.
CPC ........... *G01N 29/07* (2013.01); *G01N 29/043* (2013.01); *A61B 8/15* (2013.01); *G01N 2291/0422* (2013.01)

(58) Field of Classification Search
CPC .... G01N 29/07; G01N 29/043; G01N 29/032; G01N 29/0654; G01N 29/46;
(Continued)

(56) References Cited

U.S. PATENT DOCUMENTS

| | | | |
|---|---|---|---|
| 4,817,614 A | 4/1989 | Hassler et al. | |
| 5,720,289 A | 2/1998 | Wright et al. | |

(Continued)

FOREIGN PATENT DOCUMENTS

| | | |
|---|---|---|
| FR | 2 815 717 A1 | 4/2002 |
| WO | 2020/016250 A1 | 1/2020 |

OTHER PUBLICATIONS

French Search Report for French Patent Application No. 20 09314 dated Apr. 23, 2021, 2 pages.
(Continued)

*Primary Examiner* — Jacques M Saint Surin
(74) *Attorney, Agent, or Firm* — Merchant & Gould P.C.

(57) ABSTRACT

Method for ultrasonic characterization of a medium, comprising generating a series of incident ultrasonic waves, generating an experimental reflection matrix $R_{ui}(t)$ defined between the emission basis (i) as input and a reception basis (u) as output, and determining a focused reflection matrix $RFoc(r_{in}, r_{out}, \delta t)$ of the medium between an input virtual transducer $(TV_{in})$ calculated based on a focusing as input to the experimental reflection matrix and an output virtual transducer $(TV_{out})$ calculated based on a focusing as output from the experimental reflection matrix, the responses of the output virtual transducer $(TV_{out})$ being obtained at a time instant that is shifted by an additional delay $\delta t$ relative to a
(Continued)

time instant of the responses of the input virtual transducer ($TV_{in}$).

14 Claims, 14 Drawing Sheets

(58) Field of Classification Search
CPC ....... G01N 29/262; G01N 2291/02466; G01N 2291/0422; A61B 8/13; A61B 8/15; G01S 7/52026; G01S 7/52036; G01S 7/52046; G01S 7/52049; G01S 15/8915; G10K 11/34
USPC .......................................................... 73/597
See application file for complete search history.

(56) References Cited

U.S. PATENT DOCUMENTS

| | | | | |
|---|---|---|---|---|
| 8,915,852 | B2* | 12/2014 | Franceschini | A61B 5/14535 367/87 |
| 9,389,204 | B2* | 7/2016 | Cloutier | A61B 8/13 |
| 9,952,321 | B2* | 4/2018 | Fink | A61B 8/42 |
| 11,103,216 | B2* | 8/2021 | Bercoff | A61B 8/463 |
| 2004/0054282 | A1 | 3/2004 | Aubry et al. | |
| 2022/0082527 | A1* | 3/2022 | Lambert | G01S 7/52026 |
| 2022/0082693 | A1* | 3/2022 | Lambert | G01S 7/52036 |
| 2022/0084496 | A1* | 3/2022 | Lambert | G10K 11/346 |

OTHER PUBLICATIONS

Lambert, W. et al., "Distortion matrix approach for ultrasound imaging of random scattering media", ARXIV.Org, Cornell University Library (XP081681326 A), 1-24 (Jun. 2020).
Lambert, W. et al., "Reflection matrix approach for quantitative imaging of scattering media", ARXIV.Org, Cornell University Library (XP081680768 A), 1-18 (Jun. 2020).
Mallart, R. et al., "The van Cittert-Zernike theorem in pulse echo measurements", J. Acoust. Soc. Am., 90(5): 2718-2727 (Nov. 1991).
Montaldo, G. et al., "Coherent Plane-Wave Compounding for Very High Frame Rate Ultrasonography and Transient Elastography", IEEE Transactions on Ultrasonics, Ferroelectrics, and Frrequence Control, 56(3): 489-206 (Mar. 2009).
Rodriguez-Molares, A. et al., "Specular beamforming", IEEE Transactions on Ultrasonics Ferroelectrics and Frequence Control, 1-13 (May 2017).
Robert, J. et al., "Green's function estimation in speckle using the decomposition of the time reversal operator: Application to aberration correction i medical imaging", J. Acoust. Soc. Am., 123(2): 866-877 (Feb. 2008).

* cited by examiner

METHOD AND SYSTEM FOR ULTRASONIC CHARACTERIZATION OF A MEDIUM

CROSS-REFERENCE TO RELATED APPLICATION

This application claims benefit of Application Serial No. 20 09314, filed 15 Sep. 2020 in France and which application is incorporated herein by reference. To the extent appropriate, a claim of priority is made to the above disclosed application.

INTRODUCTION

In the field of acoustic imaging, it is desirable to characterize a totally or partially unknown environment by actively probing it using ultrasonic waves. This is the principle of the ultrasound machine used in medical imaging.

The resolution of an acoustic imaging system can be defined as the capacity for discerning the small details of an object. In principle, an acoustic imaging system is limited by diffraction, and the theoretical resolution is given by $\lambda/2$ (where $\lambda$ is the wavelength of sound in the medium), or by the finite angular aperture of the detector. In practice, however, the resolution is often degraded by variations in the speed of sound when the propagation medium is heterogeneous.

In fact, most of the time in acoustic imaging, the medium is considered to be homogeneous, with a constant speed of sound $c_0$. However, the assumption of a homogeneous environment does not always apply. For example, in the case of ultrasound of the liver, the probe is placed between the patient's ribs. The acoustic waves travel through layers of fat and muscle before reaching the target organ. The soft tissues each have different mechanical properties. The speed of sound is therefore far from homogeneous, and it can vary, for example, between 1450 m/s for adipose tissue and 1600 m/s for the liver. The variations in the speed of sound cause a different phase shift in the waves depending on the areas they are propagating through. This results in an aberration of the acoustic wavefront which leads to distortion of the resulting ultrasound image, and therefore a degradation of its resolution and contrast. These aberrations can be such that they do not allow reconstructing a reliable image, compromising the results, for example during a medical examination.

SUMMARY

According to a first aspect, this description relates to a method for ultrasonic characterization of a medium in order to locally determine a preferred direction of anisotropy of scatterers in the medium, the method comprising:

- a step of generating a series of incident ultrasonic waves $(US_{in})$ in an area of said medium, by means of an array (10) of transducers (11), said series of incident ultrasonic waves being an emission basis (i); and
- a step of generating an experimental reflection matrix $R_{ui}(t)$ defined between the emission basis (i) as input and a reception basis (u) as output;
- a step of determining a focused reflection matrix $RFoc(r_{in}, r_{out}, \delta t)$ which comprises responses of the medium between an input virtual transducer $(TV_{in})$ of spatial position $r_{in}$ and an output virtual transducer $(TV_{out})$ of spatial position $r_{out}$, the responses of the output virtual transducer $(TV_{out})$ being obtained at a time instant that is shifted by an additional delay $\delta\tau$ relative to a time instant of the responses of the input virtual transducer $(TV_{in})$,
- a step of determining a wavefront image for the input virtual transducer $(TV_{in})$ and for an additional delay interval, said wavefront image being determined as a function of the speed of sound $c_0$ in the medium, and said wavefront image being determined based on:
  - the focused reflection matrix $RFoc(r_{in}, r_{out}, \delta t)$ and
  - a ballistic propagation relation of the type $\delta t(\Delta r_{out}) = -\mathrm{sign}(\Delta z_{out}) \cdot |\Delta r_{out}|/c_0$, which makes it possible to extract values from the focused reflection matrix in order to construct the wavefront image, and where:
    $\delta t$ is the additional delay,
    $|\Delta r_{out}|$ is the modulus of the vector between the input virtual transducer $(TV_{in})$ and the output virtual transducer $(TV_{out})$, with $\Delta r_{out} = r_{out} - r_{in}$,
    $\Delta z_{out}$ is the component along a depth axis Z of the spatial position vector $\Delta r_{out}$.
- a step of determining a preferred direction of the focal spot in the wavefront image by image processing said wavefront image.

With these arrangements, the method advantageously makes it possible to probe the medium locally at any point and in any direction and with any time shift relative to a ballistic propagation time of the ultrasonic wave in the medium.

This method then makes it possible to determine a wavefront image which represents the propagation towards a focusing point, and which makes it possible to estimate the focusing quality. It is then possible to deduce information from this wavefront image about the main direction of the focal spot, which is representative of a preferred or main direction of local anisotropy of the medium. This information is for example highly representative of the local inclination of muscle fibers in the case of an imaging of a mammalian muscle. In addition, this anisotropy information can also be representative of a local lesion.

In various embodiments of the method according to this disclosure, recourse may optionally be made to one or more of the following arrangements.

According to one variant, the image processing comprises extracting the outline of the focal spot by a threshold at a level lower than the maximum value in the wavefront image, said outline serving to determine the preferred direction of the focal spot.

According to one variant:
- the wavefront image $U(r_{in}, \Delta x_{out}, \Delta z_{out})$ is converted from a reference system in Cartesian coordinates to a reference system in polar coordinates $U(r_{in}, \Delta s_{out}, \Delta\phi_{out})$.
- the values of said wavefront image in the reference system in polar coordinates are summed, over a plurality of radial distance deviation values $\Delta s_{out}$, to obtain an angular sensitivity function $f(r_{in}, \Delta\phi_{out})$ for a plurality of angular values $\Delta\phi_{out}$,
- the optimum angular value $\Delta\phi^{max}_{out}(r_{in})$ corresponding to the maximum of the angular sensitivity function is determined, said optimum angular value $\Delta\phi^{max}_{out}(r_{in})$ corresponding to the preferred direction of the focal spot associated with the input virtual transducer $TV_{in}$.

According to one variant, the preferred direction is corrected by an angle of view of the point of spatial position $r_{in}$ of the input virtual transducer $(TV_{in})$ as viewed from the array of transducers (10).

According to one variant, the preferred direction is corrected by the formula:

$$\gamma_{out}(r_{in}) = -2(\Delta\phi_{out}^{max*}(r_{in}) - \theta_{out}(r_{in}))$$

where:
$\Delta\phi_{out}^{max}(r_{in})$ is the value of the preferred direction,
$\theta_{out}(r_{in})$ is the correction of the angle of view,
$\gamma_{out}(r_{in})$ is the angular anisotropy value.

According to one variant, the correction of the angle of view is:

$$\theta_{out}(r_{in}) = \frac{1}{\sum_{u_{out}^-}^{u_{out}^+} \cos(\theta_{out}(r_{in}))} \sum_{u_{out}^-}^{u_{out}^+} \theta_{out}(r_{in})\cos(\theta_{out}(r_{in}))$$

with $$\theta_{out}(r_{in}) = a\tan\left(\frac{u_{out} - x_{in}}{z_{in}}\right)$$

where:
$u_{out}^\pm(r)$ are the maximum and minimum values of positions of transducers in the array.

According to one variant:
the roles of the input virtual transducer(s) and of the output virtual transducer(s) are reversed in order to determine a preferred direction with respect to an output virtual transducer, and
the preferred direction with reference to the input virtual transducer and the preferred direction with reference to the output virtual transducer are combined to obtain an improved preferred direction.

According to one variant:
the roles of the input virtual transducer(s) and of the output virtual transducer(s) are reversed in order to determine an angular anisotropy value with respect to an output virtual transducer $\gamma_{out}(r_{out})$, and
the angular anisotropy value with reference to the input virtual transducer $\gamma_{out}(r_{in})$ and the angular anisotropy value with reference to the output virtual transducer $\gamma_{out}(r_{out})$ are combined to obtain an improved angular anisotropy value.

According to one variant:
between the step of determining a wavefront image and the step of determining the preferred direction of the focal spot, a step of improving the wavefront image is performed in which a linear combination of a set of wavefront images corresponding to a coherence area is carried out, each wavefront image being obtained between a selected input virtual transducer ($TV_{in}$) of a different spatial position $r_{in}$, and output virtual transducers ($TV_{out}$) of spatial position $r_{out}$ such that $r_{out} = \Delta r_{out} + r_{in}$, with $\Delta r_{out}$ being predefined and identical for all wavefront images of the set, and the selected input virtual transducers being close to each other, in order to obtain an improved wavefront image associated with a reference input virtual transducer ($TV_{in,ref}$), this reference input virtual transducer ($TV_{in,ref}$) being characteristic of the input virtual transducers of the set of wavefront images used and associated with the chosen coherence area ZC, and
in the step of determining a preferred direction of the focal spot, the improved wavefront image is used instead of the wavefront image, the preferred direction of the focal spot is relative to the spatial position of the reference input virtual transducer $TV_{in,ref}$.

According to one variant, the linear combination is determined by calculating the singular value decomposition (SVD) of the set of wavefront images in order to obtain a singular vector ($W_1$) associated with the singular value of greatest absolute value of the singular value decomposition, this singular vector ($W_1$) then being the improved wavefront image corresponding to said reference input virtual transducer ($TV_{in,ref}$) and for the same additional delays $\delta t$.

According to one variant, in the step of determining the focused reflection matrix:
the calculation of the responses of the input virtual transducer ($TV_{in}$) corresponds to a focusing process at input based on the experimental reflection matrix $R_{ui}(t)$ which uses an outward time-of-flight of the waves between the emission basis and the input virtual transducer ($TV_{in}$) to create an input focal spot at spatial position $r_{in}$,
the calculation of the responses of the output virtual transducer ($TV_{out}$) corresponds to a focusing process at output based on the experimental reflection matrix $R_{ui}(t)$ which uses a return time-of-flight of the waves between the output virtual transducer ($TV_{out}$) and the transducers of the reception basis u, to create an output focal spot at spatial position $r_{out}$,
the additional delay $\delta t$ being a time lag added to the outward and return times-of-flight during the focusing processes.

According to one variant, the focused reflection matrix is calculated by the following formula:

$$RFoc(r_{in}, r_{out}, \delta t) = \frac{1}{N_{in}N_{out}} \sum_{i_{in}} \sum_{u_{out}} R_{ui}(u_{out}, i_{in}, \tau(r_{in}, r_{out}, u_{out}, i_{in}, \delta t))$$

where
$N_{in}$ is the number of elements of the emission basis (i),
$N_{out}$ is the number of elements of the reception basis (u) at output,
$R_{ui}(t)$ is the experimental reflection matrix, in which $R_{ui}(u_{out}, i_{in}, \tau(r_{in}, r_{out}, u_{out}, i_{in}, \delta t))$ is the element of the experimental reflection matrix $R_{ui}(t)$ recorded by the transducer of spatial position $u_{out}$ following the emission of index $i_{in}$ in the emission basis and at time $\tau$,
$\tau$ is a time which is the sum of the outward time-of-flight $\tau_{in}$ of the ultrasonic wave between the transducers of the emission basis (i) and the input virtual transducer ($TV_{in}$) of spatial position $r_{in}$, and of the return time-of-flight $\tau_{out}$ of the ultrasonic wave between the output transducer ($TV_{out}$) of spatial position $r_{out}$ and the transducers of the reception basis u, and of the additional delay $\delta t$, as explained by the following formula:

$$\tau(r_{in}, r_{out}, u_{out}, i_{in}, \delta t) = \tau_{in}(r_{in}, i_{in}) + \tau_{out}(r_{out}, u_{out}) + \delta t$$

According to a second aspect, this description relates to a system for ultrasonic characterization of a medium in order to locally determine a preferred direction of anisotropy of scatterers in the medium, and configured for implementing methods for ultrasonic characterization as described above. The system for ultrasonic characterization according to the second aspect comprises:
an array of transducers that are suitable for generating a series of incident ultrasonic waves in an area of the medium, and for recording the ultrasonic waves backscattered by said area as a function of time; and
a calculation unit associated with the array of transducers and suitable for implementing the method according to the first aspect.

According to another aspect, this description relates to a method for ultrasonic characterization of a medium in order to locally determine a preferred direction of anisotropy of scatterers in the medium, the method including:

generating a series of incident ultrasonic waves ($US_{in}$) in an area of said medium, by means of an array of transducers, said series of incident ultrasonic waves being an emission basis (i);

generating an experimental reflection matrix $R_{ui}(t)$ defined between the emission basis (i) as input and a reception basis (u) as output;

determining a focused reflection matrix $RFoc(r_{in}, r_{out}, \delta t)$ which comprises responses of the medium between an input virtual transducer ($TV_{in}$) of spatial position $r_{in}$ and an output virtual transducer ($TV_{out}$) of spatial position $r_{out}$, the responses of the output virtual transducer ($TV_{out}$) being obtained at a time instant that is shifted by an additional delay $\delta t$ relative to a time instant of the responses of the input virtual transducer ($TV_{in}$), determining a wavefront image for the input virtual transducer ($TV_{in}$) and for an additional delay interval, said wavefront image being determined as a function of the speed of sound $c_0$ in the medium, and said wavefront image being determined based on:

the focused reflection matrix $RFoc(r_{in}, r_{out}, \delta t)$ and a ballistic propagation relation of the type $\delta t(\Delta r_{out}) = -\mathrm{sign}(\Delta z_{out}) \cdot |\Delta r_{out}|/c_0$, which makes it possible to extract values from the focused reflection matrix in order to construct the wavefront image, and where:

$\delta t$ is the additional delay, $\Delta r_{out}$ is the modulus of the vector between the input virtual transducer ($TV_{in}$) and the output virtual transducer ($TV_{out}$), with $\Delta r_{out} = r_{out} - r_{in}$, $\Delta z_{out}$ is the component along a depth axis Z of the spatial position vector $\Delta r_{out}$; and determining a preferred direction of the focal spot in the wavefront image by image processing said wavefront image.

According to another aspect, this description relates to a system for ultrasonic characterization of a medium in order to determine a temporal and local characterization of an ultrasonic focusing, the system including:

an array of transducers that are suitable for generating a series of incident ultrasonic waves in an area of the medium, and for recording the ultrasonic waves backscattered by said area as a function of time;

one or more processors; and a memory storing instructions that, when executed by the one or more processors, cause the system to perform operations including:

generating a series of incident ultrasonic waves ($US_{in}$) in an area of said medium, by means of an array of transducers, said series of incident ultrasonic waves being an emission basis (i);

generating an experimental reflection matrix $R_{ui}(t)$ defined between the emission basis (i) as input and a reception basis (u) as output;

determining a focused reflection matrix $RFoc(r_{in}, r_{out}, \delta t)$ which comprises responses of the medium between an input virtual transducer ($TV_{in}$) of spatial position $r_{in}$ and an output virtual transducer ($TV_{out}$) of spatial position $r_{out}$, the responses of the output virtual transducer ($TV_{out}$) being obtained at a time instant that is shifted by an additional delay $\delta t$ relative to a time instant of the responses of the input virtual transducer ($TV_{in}$), determining a wavefront image for the input virtual transducer ($TV_{in}$) and for an additional delay interval, said wavefront image being determined as a function of the speed of sound $c_0$ in the medium, and said wavefront image being determined based on:

the focused reflection matrix $RFoc(r_{in}, r_{out}, \delta t)$ and a ballistic propagation relation of the type $\delta t(\Delta r_{out}) = -\mathrm{sign}(\Delta z_{out}) \cdot |\Delta r_{out}|/c_0$, which makes it possible to extract values from the focused reflection matrix in order to construct the wavefront image, and where:

$\delta t$ is the additional delay, $\Delta r_{out}$ is the modulus of the vector between the input virtual transducer ($TV_{in}$) and the output virtual transducer ($TV_{out}$), with $\Delta r_{out} = r_{out} - r_{in}$, $\Delta z_{out}$ is the component along a depth axis Z of the spatial position vector $\Delta r_{out}$; and determining a preferred direction of the focal spot in the wavefront image by image processing said wavefront image.

BRIEF DESCRIPTION OF FIGURES

Other features and advantages of the technique presented above will be apparent from reading the detailed description below, presented in a non-limiting manner for illustrative purposes, made with reference to the figures in which.

In the various embodiments which will be described with reference to the figures, similar or identical elements bear the same references, unless otherwise specified.

DETAILED DESCRIPTION

In the following detailed description, only certain embodiments are described in detail in order to ensure the clarity of the description, but these examples are not intended to limit the general scope of the principles that emerge from this description.

The various embodiments and aspects described in this description can be combined or simplified in multiple ways. In particular, the steps of the various methods can be repeated, inverted, and/or executed in parallel, unless otherwise specified.

This description relates to methods and systems for ultrasonic characterization of a medium, and applies in particular to the medical imaging of living or non-living tissues. The medium is for example a heterogeneous medium which one seeks to characterize in order for example to identify and/or characterize the heterogeneities. Optionally, these methods and systems can be applied to non-destructive testing of products, such as metal parts or the like. These characterization techniques are thus non-invasive in the medium, which is then preserved.

Figure 1A:
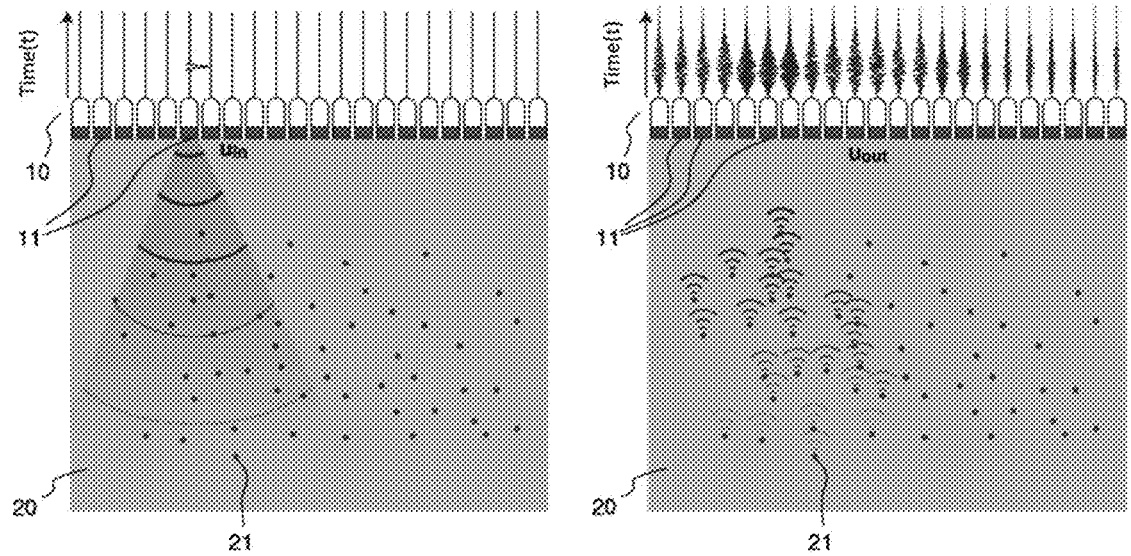
FIGS. 1A to 1C illustrate emission/reception mechanisms for ultrasound imaging and quantification.
Figure 1B:
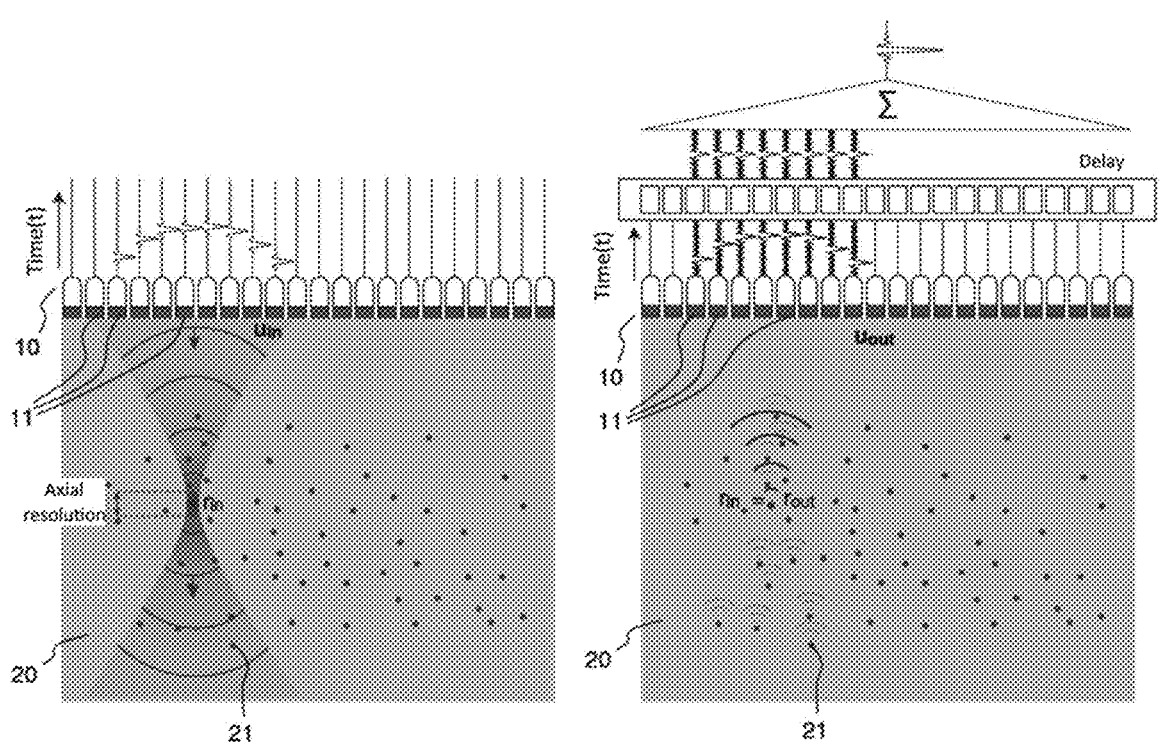
Figure 1C:
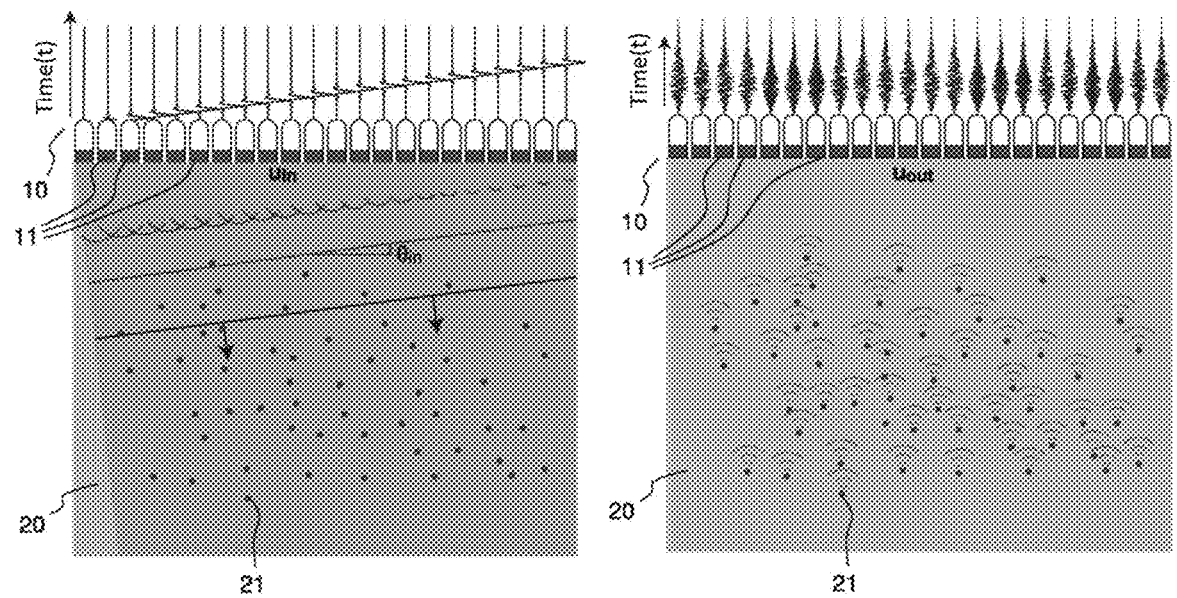

As illustrated in FIGS. 1A-1C, ultrasound methods use an array 10 of piezoelectric transducers 11 which can emit and/or receive ultrasonic pulses independently. The position of each transducer is identified by the vector u. When such an array is placed facing a medium that one wishes to study, the medium can be insonified and imaged in various ways.

A first way to generate an ultrasound image of the medium to be studied is to emit an ultrasonic pulse from one of the transducers of the array whose position is identified by the vector $u_{in}$ (FIG. 1A, left diagram). This results in a divergent cylindrical (or spherical) incident wave for a 1D (or 2D) array of transducers. This wave is reflected by the scatterers 21 of the medium 20 and the backscattered field is recorded as a function of time by each of the transducers 11 (FIG. 1A, right diagram). By repeating this operation with each transducer successively used as a source, the set of impulse responses $R(u_{out}, u_{in}, t)$ between each transducer is measured, where the vector $u_{out}$ denotes the position of the detector. These responses form the reflection matrix $R_{uu}(t)$ expressed in the basis of the transducers. The advantage of such a measurement lies in the fact that this matrix contains all the information about the analyzed medium, it then being possible to apply a set of matrix operations to it for the purposes of imaging the medium, for example. On the other hand, such acquisition assumes that the medium remains fixed for the duration of the measurements, which can be very difficult in the case of in-vivo use. In addition, the energy emitted by a single piezoelectric element is low, which can result in a poor signal-to-noise ratio.

Other methods are known for generating an image of the medium to be analyzed, in which focused emissions are carried out using a beamforming technique. As shown in FIG. 1B, left diagram, these methods consist of applying to the transducers 11 a set of appropriate delays, based on a homogeneous speed model, in order to correct the travel times of the waves so that all the pulses arrive together at the target focal point at position $r_{in}$. The assumed speed of sound that is adopted will be denoted $c_0$. Due to the physical limitations of diffraction, the ultrasound emitted is concentrated in an area bounded by the aperture of the ultrasound probe. In order to construct an ultrasound image, a focusing step is also performed at reception. The set of echoes captured by the elements 11 of the array 10 are then processed to simulate the effect of a lens at reception, as described in FIG. 1B, right diagram. The signals received by the transducers are time-shifted to bring them back into phase. These delays are identical to those applied at emission. In the emission phase, all signals interfere at the point of position $r_{in}$. At reception, the signals coming from this same point $r_{out}=r_{in}$ interfere electronically by summation of the signals at ballistic time $t=(\|u_{out}-r_{in}\|+\|u_{in}-r_{in}\|)/c_0$. This summation gives the final result of the focusing at reception. The method illustrated in FIG. 1B, known as the method of confocal dual focusing at transmission and reception, makes it possible to directly image the reflectivity of the medium with a lateral resolution limited by diffraction, an excellent axial resolution only limited by the duration of the initial pulse, and excellent contrast. However, this method is time-consuming because it requires physically focusing at emission at each of the points of the medium or at least at a given depth, on each of the rows of the image.

Another imaging technique consists of generating an image of the medium by insonifying the medium with a series of plane waves. FIG. 1C illustrates the principle of this so-called plane wave ultrasound, described for example in the article by G. Montaldo et al. "Coherent plane-wave compounding for very high frame rate ultrasonography and transient elastography" (IEEE Trans. Ultrason., Ferroelect. Freq. Control 56 489-506, 2009), the disclosure of which is hereby incorporated by reference herein in its entirety. Delays are applied to each signal at emission (FIG. 1C, left diagram) to form a wavefront inclined at an angle $\theta_{in}$ relative to the array of transducers 10. At reception (FIG. 1C, right diagram), the field backscattered by the medium, $R(u_{out}, \theta_{in}, t)$ is measured by all the position sensors $u_{out}$ for a series of incident plane waves in which the angle of incidence $\theta_{in}$ is varied. The set of these responses forms a reflection matrix $R_{u\theta}(t)$ defined between the spatial Fourier basis (or plane wave basis) as input and the basis of the transducers as output. Once this matrix is recorded, the signals are time-shifted before being coherently summed in order to digitally focus the data at emission and at reception for each point of position $r_{in}$. The number of data captures necessary to form an ultrasound image is thus advantageously reduced compared to standard ultrasound (focused emissions), and this is true for the same level of contrast and resolution of the ultrasound image.

Figure 2:
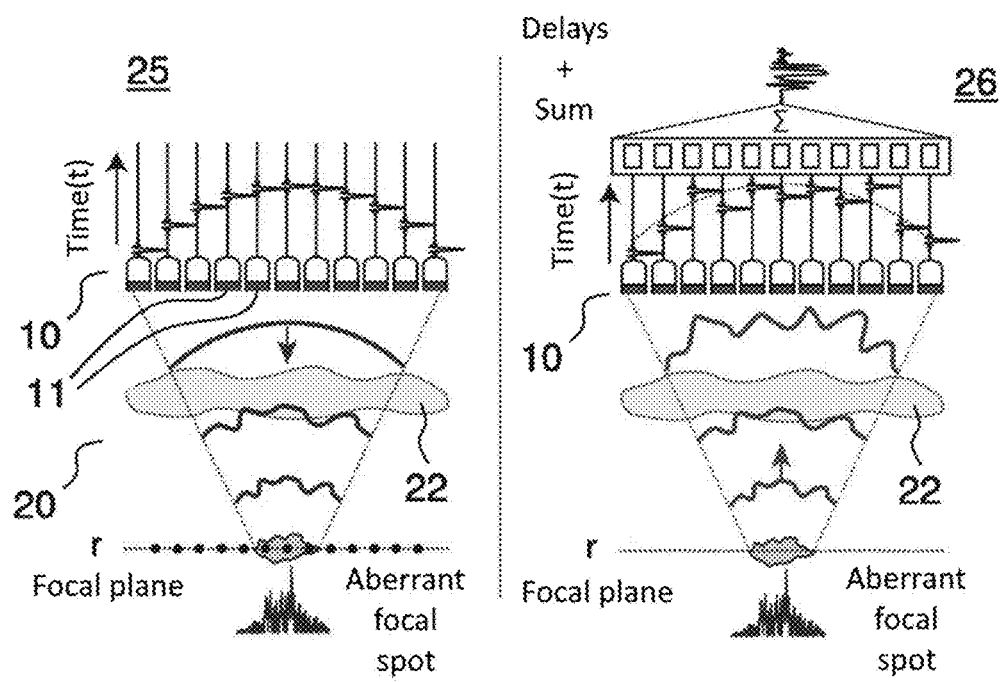
FIG. 2 illustrates the impact of aberrations in ultrasound imaging.

FIG. 2 illustrates the influence of environmental aberrations on conventional ultrasound imaging methods (FIGS. 1A to 1C). These aberrations appear when the speed of sound in the medium c(r) does not correspond to the assumption of a homogeneous medium with a constant speed of sound $c_0$. The delays initially determined on the basis of this assumption and to be applied to each of the transducers of the array at transmission and at reception are then not optimal for evaluating an image of the medium. In FIG. 2, an aberrating layer 22 induces a distortion of the incident wavefront. At emission or excitation, step 25, the delay rules used do not allow the acoustic energy to be concentrated in an area bounded by the diffraction limits, areas usually called the focal spot. At reception, in step 26, the delay rules used do not allow correctly selecting the ultrasonic signals originating from the focal point of the medium, and intermix the signals originating from an equally aberrant focal spot. This results in a double aberration in the image construction process, which greatly degrades its resolution. New delay rules can then be recalculated in order to compensate for the effect of the aberrating layer, for example by adding an additional delay rule to the delays generally used in beamforming.

However, these aberration corrections do not completely correct either these aberrations or the resolution degradation. There is a need to better estimate the focusing quality in the medium.

The document "The van Cittert-Zernike theorem in pulse echo measurements" (Raoul Mallart and Mathias Fink, J. Acoust. Soc. Am. 90 (5), November 1991), the disclosure of which is hereby incorporated by reference herein in its entirety, studied the statistical properties of the field reflected by a random medium under simple scattering conditions. In particular, it has been shown that for a focused incident wave, the spatial covariance of the reflected field is proportional, from the far field, to the Fourier transform of the transmitting aperture function. In other words, this theorem explains that the study of the statistical properties of the reflected field in the far field makes it possible to determine the focusing quality of the incident wave in the medium.

However, this approach only provides an overall average estimate of the resolution of an ultrasound image, because it requires statistically averaging the correlations of the reflected field over a large number of implementations of disorder, i.e. over a large number of focus points of the incident wave. It does not allow obtaining a precise and local assessment of the focusing quality at each point of the image. Moreover, this approach is only valid under simple scattering conditions.

Figure 3:
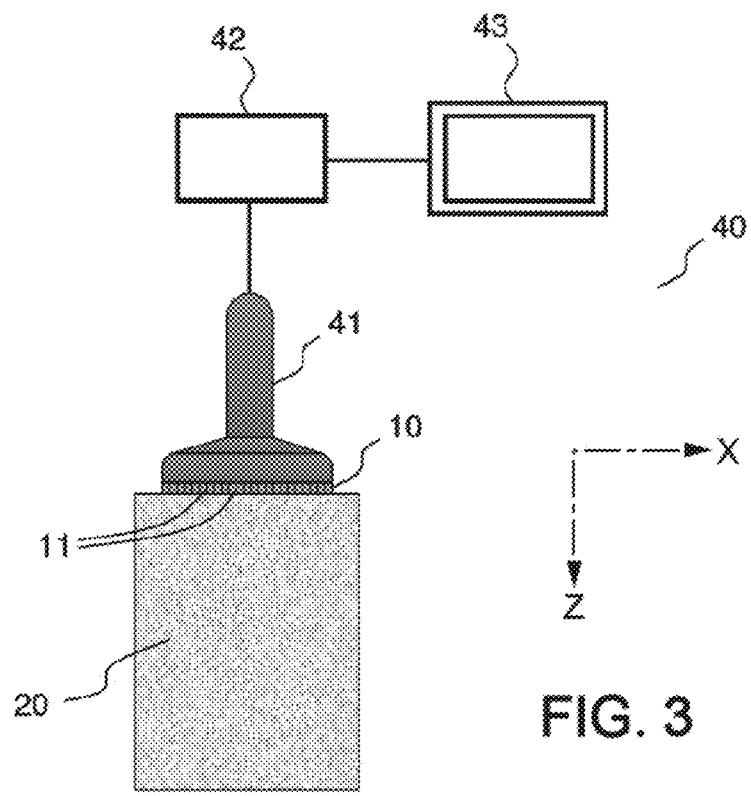
FIG. 3 illustrates an example of a system for ultrasonic characterization, for implementing the methods for ultrasonic characterization according to this description.

FIG. 3 illustrates an example of a system 40 for ultrasonic characterization, for implementing methods for ultrasonic characterization of a medium such as a heterogeneous medium 20, according to this description. The system 40 comprises at least one array 10 of transducers 11, for example a linear or two-dimensional or matrix array; the transducers are for example piezoelectric ultrasonic transducers which may be in the conventional form of a rigid bar brought into direct or indirect contact with the medium 20. The array of transducers is for example part of a probing device 41 (usually called probe); the array of transducers is connected to a special- or general-purpose computer or calculation unit 42 (which may include one or more processors and a memory), which itself may be connected to or associated with a display device 43; the calculation unit emits and records electrical signals to and/or from each of the transducers 11. The ultrasonic transducers then convert these electrical signals into ultrasonic waves and vice versa. "Connection" or "link" between the probing device 41, the calculation unit 42, and the display device 43, is understood to mean any type of wired connection, electrical or optical, or any type of wireless connection using any protocol such as WiFi™, Bluetooth™, or others. These connections or links are one-way or two-way.

The calculation unit 42 is configured to implement calculation or processing steps or operations, in particular to implement the steps or operations of methods according to this description. By convention, a spatial reference system for the medium 20 is defined by taking a first axis X and a second axis Z perpendicular to the first. For simplicity, the first axis X corresponds to the transverse direction in which the transducers 11 are aligned for a linear array, and the second axis Z corresponds to the depth of the medium 20 relative to this array of transducers 11. This definition can be adapted to the context and thus for example extended to a three-axis spatial reference system in the case of a two-dimensional array 10.

In FIG. 3, as in the rest of the description, reference is made to an array of transducers for emission and reception, it being understood that, in a more general case, several arrays of transducers could be used simultaneously. Similarly, an array can consist of one (1) to N transducers, of identical type or of different kinds. The transducers can be both transmitter and receiver, or only transmitter for some and only receiver for others.

The transducer array serves, for example, both as a transmitter and as a receiver, or is composed of several sub-arrays of transducers, some being dedicated to emission of ultrasonic waves, others to reception. The term "array of transducers" is understood to mean at least one transducer, an aligned or non-aligned series of transducers, or a matrix of transducers.

In this description, when reference is made to computational or processing steps or operations, in particular for implementing steps or operations of the methods, it is understood that each computational or processing step or operation can be implemented by software, hardware, firmware, microcode, or any suitable combination of such technologies or related technologies. When software is used, each computational or processing step or operation may be implemented by computer program instructions or code which for example can be interpreted or executed. These instructions may be stored in or transmitted to a storage medium readable by a computer (or calculation unit) and/or be executed by a computer (or calculation unit) in order to implement these computational or processing steps or operations.

Analysis of a Point in the Medium by Focused Reflection Matrix

This description describes methods and systems for ultrasonic characterization of a medium. In practical cases, the medium is assumed to be heterogeneous. These methods and systems are based on definitions shown in FIG. 4:

In examples, we define in the medium:
a first point P1 of spatial position $r_{in}$ in the spatial reference system of the medium,
a second point P2 of spatial position $r_{out}$ in the spatial reference system of the medium.

These spatial positions $r_{in}$ and $r_{out}$ may be indicated in bold herein, to signify that these elements are position vectors, vectors taken in the spatial reference system of the medium (X, Z). Other representations and definitions for the positions of points are possible and accessible to any specialist in the ultrasound profession.

These two points P1 and P2 are chosen to be a short distance from one another, meaning a few millimeters from one another, and for example twenty (20) millimeters or less, at ultrasound frequencies.

Figure 4:
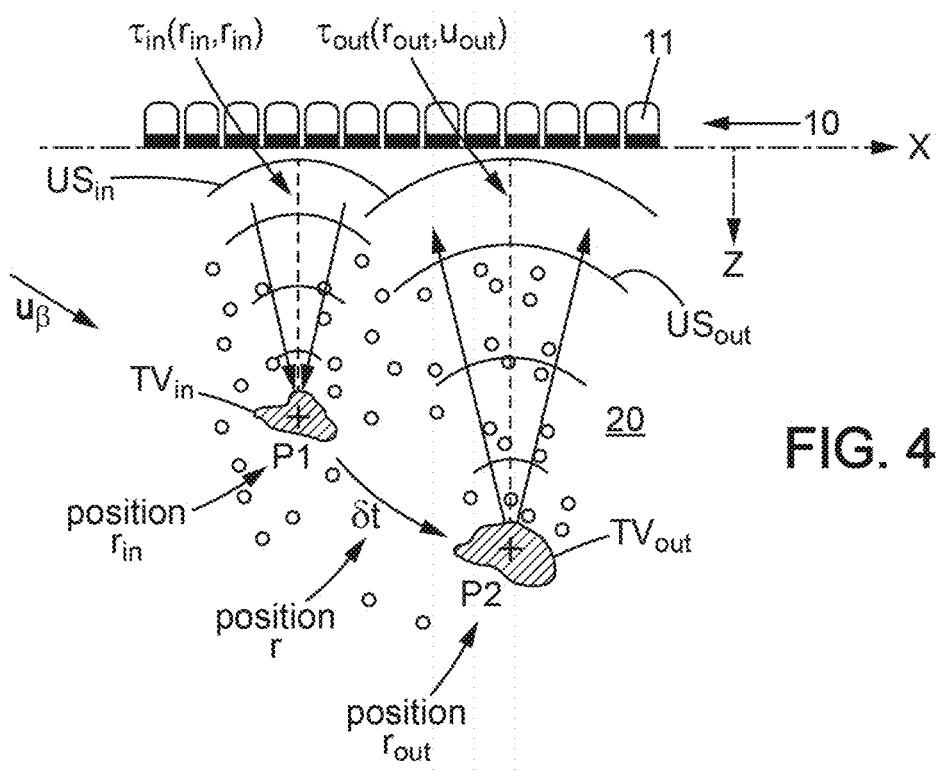
FIG. 4 illustrates the definitions used in the method for ultrasonic characterization according to this description.

As represented in FIG. 4, the method for ultrasonic characterization implemented by the calculation unit 42 of the system 40 comprises:

generating a series of incident ultrasonic waves $US_{in}$ in an area of said medium, by means of an array 10 of transducers 11, said series of incident ultrasonic waves being an emission basis i; and generating an experimental reflection matrix $R_{ui}(t)$ defined between the emission basis i as input and a reception basis u as output;

determining a focused reflection matrix $RFoc(r_{in}, r_{out}, \delta t)$ which comprises responses of the medium between an input virtual transducer $TV_{in}$ of spatial position $r_{in}$ and an output virtual transducer $TV_{out}$ of spatial position $r_{out}$, the responses of the output virtual transducer $TV_{out}$ being obtained at a time instant shifted by an additional delay $\delta t$ relative to a time instant of the responses of the input virtual transducer $TV_{in}$.

The responses of the focused reflection matrix $RFoc(r_{in}, r_{out}, \delta t)$ correspond to an acoustic pressure field calculated at any point in the medium.

The emission basis i as input is for example a basis of waves each generated by one of the transducers 11 of the array 10 or a basis of plane waves of angular inclination θ relative to axis X, as described above in the description for FIGS. 1A to 1C.

The reception basis u is for example the basis of the transducers 11. Optionally, another reception basis can be used at reception.

Thus, generating ultrasonic waves is intended between the transmission basis i and the reception basis u. This generating ultrasound is therefore defined for any type of ultrasonic wave, focused or unfocused, such as plane waves.

In generating the matrix, the experimental reflection matrix $R_{ui}(t)$ is defined between the emission basis i as input and a reception basis u as output. This matrix contains the set of time responses of the medium, measured at time t by each transducer 11 of spatial coordinate $u_{out}$ and for each emission $i_{in}$. It is understood that the elements named with the index "in" refer to emission (i.e. input) and the elements named with the index "out" refer to reception (i.e. output). This experimental matrix can also be recorded and/or stored, for example in the memory of the calculation unit, or on any other medium, removable or not, enabling permanent or temporary storage.

More precisely, in determining the focused reflection matrix $RFoc(r_{in}, r_{out}, \delta t)$, we apply:

a focusing process at input based on the experimental reflection matrix $R_{ui}(t)$ which uses an outward time-of-flight of the waves between the emission basis (i) and the input virtual transducer $TV_{in}$ and which creates a so-called input focal spot around the first point P1 of spatial position $r_{in}$, said input focal spot corresponding to the input virtual transducer $TV_{in}$, a focusing process at output based on the experimental reflection matrix $R_{ui}(t)$ which uses a return time-of-flight of the waves between the output virtual transducer ($TV_{out}$) and the transducers of the reception basis (u) and which creates a so-called output focal spot around the second point P2 of spatial position $r_{out}$, said output focal spot corresponding to the output virtual transducer $TV_{out}$, an additional delay $\delta t$ which is a time lag added to the outward and return times-of-flight during the focusing processes.

These focusing processes at input and output in fact form a focusing process at input-output, referred to in the remainder of this description as the focusing process.

In other words, in this method for ultrasonic characterization, the input virtual transducer $TV_{in}$ corresponds to an ultrasonic "virtual source" located at spatial position $r_{in}$ in the medium, and the output virtual transducer $TV_{out}$ corresponds to an ultrasonic "virtual sensor" located at spatial position $r_{out}$. This virtual source and this virtual sensor are spatially separated by the difference in their spatial positions $\Delta r = r_{out} - r_{in}$. They are also temporally separated by the additional delay $\delta t$, which is an arbitrary and adjustable delay independent of the spatial distance $|\Delta r|$. Thus, the method is able to probe the medium around point P1 and/or point P2, spatially and/or temporally, which makes it possible to obtain new information in these two dimensions (spatial and temporal) concerning the wave propagation.

For example, a calculation of the focused reflection matrix $RFoc(r_{in}, r_{out}, \delta t)$ of the medium between the input virtual transducer $TV_{in}$ and the output virtual transducer $TV_{out}$ by said focusing processes at input and at output, is an improved beamforming method which can be expressed by the following simplified formula:

$$RFoc(r_{in}, r_{out}, \delta t) = \frac{1}{N_{in}N_{out}} \sum_{i_{in}} \sum_{u_{out}} R_{ui}(u_{out}, i_{in}, \tau(r_{in}, r_{out}, u_{out}, i_{in}, \delta t)) \quad \text{(Eq. 1)}$$

where $N_{in}$ is the number of elements of the emission basis i, $N_{out}$ is the number of elements of the reception basis u at output, $R_{ui}(t)$ is the experimental reflection matrix, in which $R_{ui}(u_{out}, i_{in}, \tau(r_{in}, r_{out}, u_{out}, i_{in}, \delta t))$ is the element of the experimental reflection matrix $R_{ui}(t)$ recorded by the transducer $u_{out}$ following emission $i_{in}$ at time $\tau$.

Time $\tau$ is the sum of the outward time-of-flight $\tau_{in}$ of the ultrasonic wave between the transducers of the emission basis i and the input virtual transducer $TV_{in}$ of spatial position $r_{in}$ (first point P1), of the return time-of-flight $\tau_{out}$ of the ultrasonic wave between the output virtual transducer $TV_{out}$ of spatial position $r_{out}$ (second point P2) and the transducers of the reception basis u, and the additional delay $\delta t$, as explained by the following formula:

$$\tau(r_{in}, r_{out}, u_{out}, i_{in}, \delta t) = \tau_{in}(r_{in}, i_{in}) + \tau_{out}(r_{out}, u_{out}) + \delta t \quad \text{(Eq. 2)}$$

The times-of-flight $\tau_{in}$ and $\tau_{out}$ are calculated from a speed of sound model. The simplest hypothesis consists of assuming a homogeneous medium with a constant speed of sound $c_0$. In this case, the times-of-flight are obtained directly, based on the distances between the transducers of the probe and the virtual transducers.

The number of elements of the emission basis $N_{in}$ is for example greater than or equal to one (1), and advantageously greater than or equal to two (2). The number of elements of the reception basis $N_{out}$ is for example greater than or equal to two (2).

This improved beamforming formula is therefore a double sum of the time responses recorded in the experimental reflection matrix $R_{ui}$: a first sum according to the emission basis i expressing a focusing at emission, and a second sum according to the reception basis u linked to a focusing at reception, this calculation being carried out for the spatial coordinates of the two points P1 and P2 (of spatial positions $r_{in}$, $r_{out}$). The result of this improved beamforming formula is therefore a time signal for these two spatial coordinates ($r_{in}$, $r_{out}$), but is also a function of the additional delay $\delta t$ between input and output, this additional delay being adjusted arbitrarily.

Such a beamforming formulation can also be supplemented by input and output weighting terms, often called reception and/or transmission apodization. The rest of the beamforming formulas can thus be supplemented with these weights by a technician skilled in this field.

The recorded experimental reflection matrix $R_{ui}(t)$ can be a "real" matrix, i.e. composed of real coefficients in the time domain, the electrical signals recorded by each of the transducers being real numbers. Alternatively variant, this matrix can be a "complex" matrix, i.e. composed of complex values, for example in the case of demodulation for in-phase and quadrature beamforming ("IQ beamforming").

We thus obtain a focused reflection matrix RFoc($r_{in}$, $r_{out}$, $\delta t$) which contains time signals. This focused reflection matrix has five (5) dimensions in the case of a linear probe; two spaces for the spatial positions $r_{in}$ and $r_{out}$, as well as the additional delay $\delta t$, which is very different and much richer in information than in the focused reflection matrices of the prior art.

In this analysis, due to the additional delay $\delta t$, the input $TV_{in}$ and output $TV_{out}$ virtual transducers are not defined at the same time instant, which makes it possible to highlight virtually the propagation of the ultrasonic wave between the first point P1 of the input virtual transducer $TV_{in}$ and the second point P2 of the output virtual transducer $TV_{out}$. This additional delay $\delta t$ can be positive or negative, which makes it possible to probe the focusing of the ultrasonic wave at the second point P2 respectively before and after a reference time instant of the paths of the ultrasonic wave in the medium.

This reference time instant is called the ballistic time $t_b$. This ballistic time is the round-trip time of the ultrasonic wave between the transducers of the emission basis i to the input virtual transducer $TV_{in}$, then between the output virtual transducer $TV_{out}$ and the transducers of the reception basis u.

This ballistic time $t_b$ is defined by the following formula:

$$t_b = (\|r_{out} - r_{out}\| + \|r_{in} - r_{in}\|)/c_0 \quad \text{(Eq. 3)}$$

where:

$c_0$ is the assumed speed of sound of the medium (speed of propagation of ultrasonic waves).

Due to these arrangements, the method makes it possible to probe the medium very locally at the second point P2 with respect to the first point P1, with an additional delay $\delta t$ between the signals coming from these two points. This local information is entirely contained in the values of the time response calculated from the focused reflection matrix RFoc($r_{in}$, $r_{out}$, $\delta t$) of the medium and can be exploited after the fact (and without any new emission and/or acquisition) to characterize each point of the medium.

It is thus possible to deduce, from this time response after beamforming, an estimate of the reflectivity of the medium by considering the absolute value of the confocal signals characterized by spatial positions that are equal at input and output $r_{in} = r_{out}$ and at zero additional delay $\delta t = 0$ (i.e. at the ballistic time without this additional delay). This estimate of the reflectivity of the medium is the value of a pixel of an ultrasound image of the medium. Thus, to construct an ultrasound image, one can scan or choose a set of spatial positions $r = r_{in} = r_{out}$ which correspond to a set of pixel positions in the ultrasound image.

The ultrasound image $I^{(0)}(r)$ can then be constructed based on the focused reflection matrix RFoc($r_{in}$, $r_{out}$, $\delta t$) by taking $r = r_{in} = r_{out}$ and $\delta t = 0$, meaning:

$$I^{(0)}(r) = \text{RFoc}(r_{in}, r_{out} = r_{in}, \delta t = 0) \quad \text{(Eq. 4)}$$

Images of Propagation Around a Point of the Medium

The method for ultrasonic characterization implemented by the calculation unit 42 of the system 40 can then be supplemented by constructing one or more propagation images based on the focused reflection matrix RFoc($r_{in}$, $r_{out}$, $\delta t$), this or these propagation images being determined for one or more values of the additional delay $\delta t$, for one input virtual transducer $TV_{in}$ (first points P1) and for a plurality of output virtual transducers $TV_{out}$ (second points P2), the output virtual transducers $TV_{out}$ being located at spatial positions $r_{out}$ around the input virtual transducer $TV_{in}$ of spatial position $r_{in}$.

In the case of a single propagation image, this propagation image is determined from the focused reflection matrix RFoc($r_{in}$, $r_{out}$, $\delta t$) for a single predetermined additional delay $\delta t$.

This propagation image represents the manner in which an ultrasonic wave propagates between the virtual transducers, and for example near the input virtual transducer, and at a time instant equal to the additional delay (time instant taken as relative with respect to the ballistic time).

The system 40 is then optionally able to display one or more propagation images on the display device 43.

The calculation unit 42 can also calculate a series of propagation images for several additional temporally successive delays, for example to construct a propagation film of the ultrasonic wave around the input virtual transducer $TV_{in}$ (first point P1). This propagation film can optionally be displayed on the display device 43 or on any other medium.

The temporally successive additional delays applied in order to construct this propagation film are applied in our example within an additional delay interval.

For example, the additional delay interval can take the form of a time span adapted to extend from the input virtual transducer $TV_{in}$ of spatial position $r_{in}$ to all of the output virtual transducers $TV_{out}$ of spatial position $r_{out}$. This additional delay interval is then for example denoted $[-\delta t_{min}, +\delta t_{max}]$, with $\delta t_{min} = z_{out}^{max} - z_{in}/c_0$ and $\delta t_{max} = z_{out}^{max} - z_{in}/c_0$, where $z_{in}$ and $z_{out}$ are respectively the depths in the positive direction of the second axis Z of the input virtual transducer $TV_{in}$ of spatial position $r_{in}$ and of the output virtual transducer $TV_{out}$ of spatial position $r_{out}$.

For example, the additional delay interval can be symmetrical around the zero value ($\delta t = 0$) and of amplitude $\delta t_{max}$, this additional delay interval being denoted $[-\delta t_{max}, +\delta t_{max}]$. For example, it can be defined by $\delta t_{max} = \max(|\Delta r|)/c_0$ for the output transducers $TV_{out}$ used for the propagation image.

Figure 5:
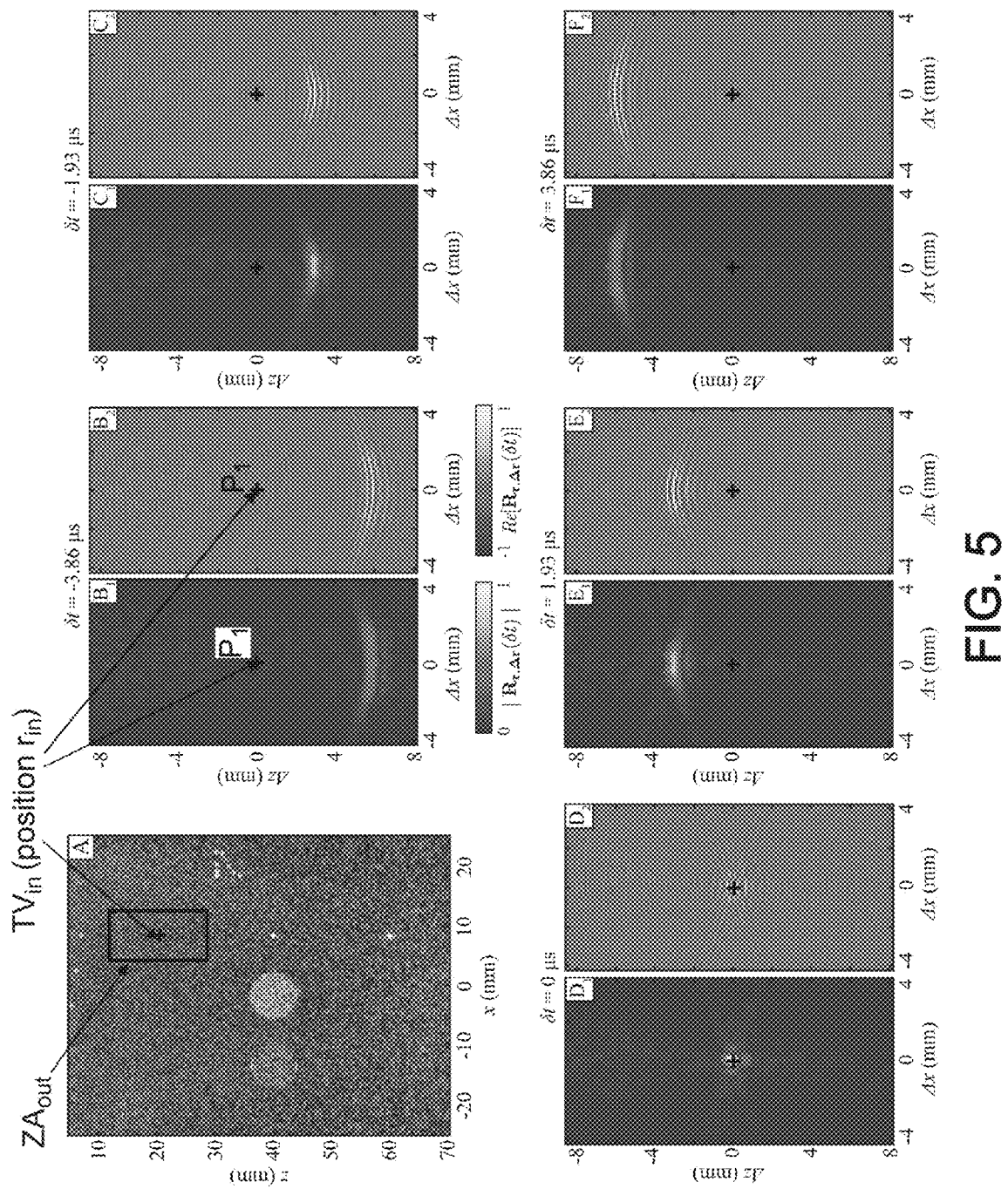
FIG. 5 shows an ultrasound image in which a position associated with an echogenic element is selected and propagation images around this position are obtained for several additional delays.

The image denoted A in FIG. 5 shows an ultrasound image of an analyzed sample medium or phantom, which comprises predetermined heterogeneities of several types. In this medium, we consider a rectangular analysis area $ZA_{out}$ (composed of second points P2 of output virtual transducers $TV_{out}$) which is scanned by calculation in order to construct one or more propagation images around the first point P1 of input virtual transducer $TV_{in}$ of spatial position $r_{in}$, here located in the medium of the analysis area $ZA_{out}$. The analysis area can be positioned at any position independently of the position of the input virtual transducer. However, it is of particular interest to have the analysis area surround the input virtual transducer.

In this reference image A, the input virtual transducer $TV_{in}$ (first point P1) is located on or near a reflecting element (echogenic target) of the medium.

The images denoted B to F in FIG. 5 are propagation images of the analysis area $ZA_{out}$ of image A in FIG. 5, for five (5) additional delay values δt. These additional delays are −3.86 μs, −1.93 μs, 0 μs, 1.93 μs, 3.86 μs in our illustrative example. Each propagation image is composed of:
- a first image of index 1 (for example $B_1$) corresponding to the amplitude of the values of the focused reflection matrix for a set of points in the analysis area $ZA_{out}$, and
- a second image of index 2 (for example $B_2$) corresponding to the real portion of the values of the focused reflection matrix for the same set of points in the analysis area $ZA_{out}$.

In these images, the level of the amplitude or the level of the real portion is represented by a grayscale for which the legend appears in images $B_1$ and $B_2$ of FIG. 5. The points or pixels of these propagation images have $\Delta r = r_{out} - r_{in}$ for the spatial position, meaning the relative position of the output virtual transducers $TV_{out}$ of spatial position $r_{out}$ with respect to the position $r_{in}$ of the input virtual transducer $TV_{in}$. In the figure illustrating this example, the coordinates on these images are denoted Δx on the abscissa and Δz on the ordinate.

These propagation images illustrate the explanations given above concerning the focused reflection matrix calculated with an additional delay δt: They make it possible to visualize the propagation of a coherent wave. In particular, for negative additional delays going towards zero, this coherent wave converges towards the first point P1 of the input virtual transducer $TV_{in}$, and is ideally concentrated and focused in a focal spot defined by the diffraction limits for zero additional delay (δt=0). This coherent wave is then divergent for positive and increasing additional delays.

This coherent wave results from a process of digital time reversal of the echoes coming from the virtual source located at the input virtual transducer of spatial position $r_{in}$ and which are measured by the transducers of the probe. By performing beamforming at reception for a set of spatial positions $r_{out}$ around the input virtual transducer of spatial position $r_{in}$, and at the various additional times δt, this illustrates the focusing at reception outside the confocal position (i.e. $r_{in} \neq r_{out}$).

As these propagation images are obtained for a first point P1 of the input virtual transducer $TV_{in}$ located on or near a reflecting element (echogenic target) of the medium, the coherent wave is easily identifiable in these propagation images and presents a good signal-to-noise ratio compared to neighboring signals.

Figure 6:
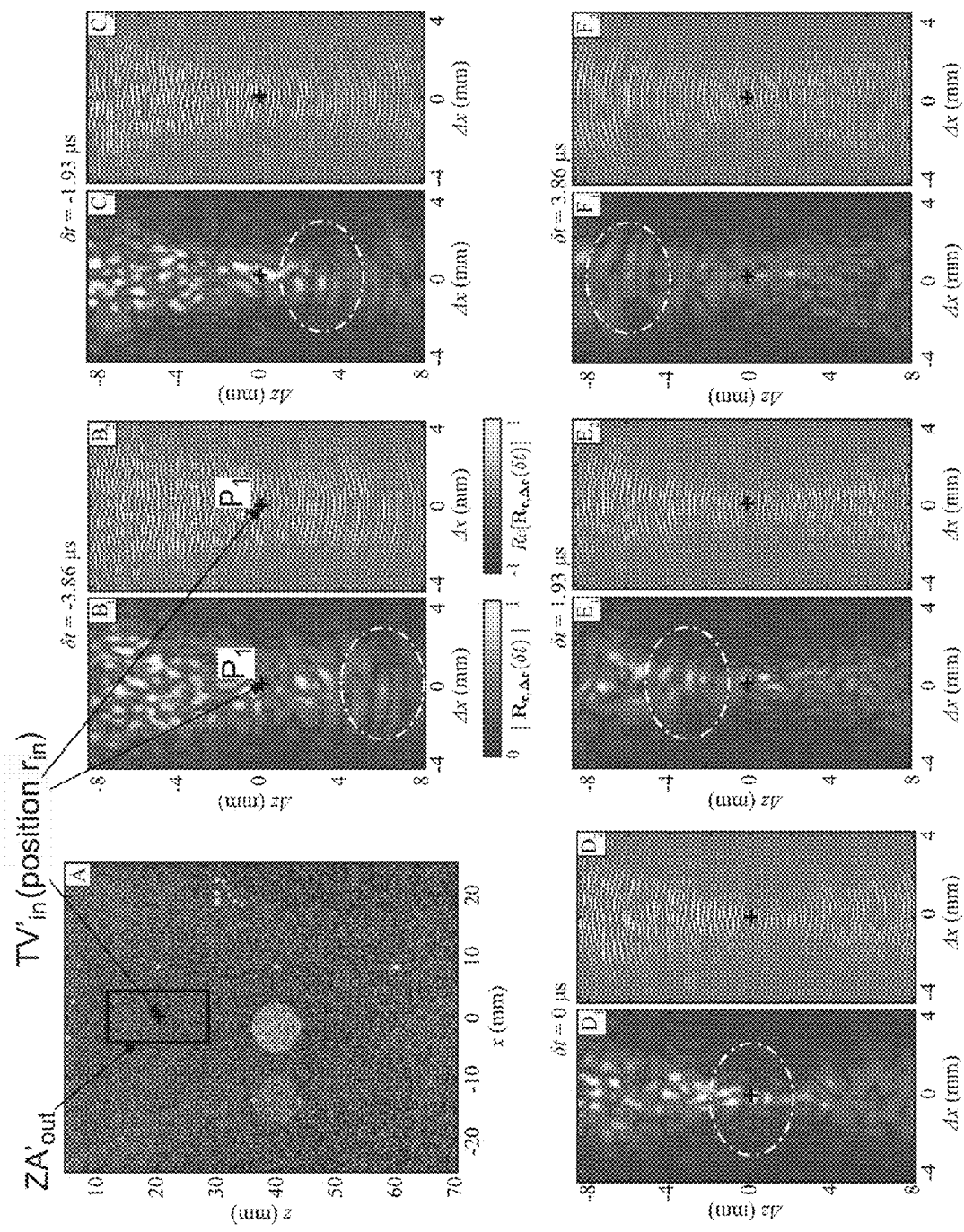
FIG. 6 shows an ultrasound image in which a position associated with a set of sub-resolution scatterers of comparable reflectivity is selected and propagation images around this position are obtained for several additional delays.

The image denoted A in FIG. 6 shows the same ultrasound image as the one in FIG. 5, but in which another rectangular analysis area $ZA'_{out}$ is considered (of the same dimensions in this example) which is scanned by calculation in order to construct propagation images around another first point P1' of input virtual transducer $TV'_{in}$ of spatial position $r_{in}$.

This other first point P1' of input virtual transducer $TV'_{in}$ is here associated with a resolution cell containing a set of sub-resolution scatterers, arranged randomly and having comparable reflectivity. At the wavelength scale, such a medium is called "ultrasound speckle" and is characterized by a random reflectivity resulting from destructive and constructive interactions between each of the sub-resolution scatterers, responsible for the granular effect of the B-mode ultrasound image.

The images denoted B to F of FIG. 6 are propagation images of this other analysis area $ZA'_{out}$ of image A in FIG. 6, for the same five additional delay values δt as for images B to F in FIG. 5.

The amplitudes and real parts of the values of the focused reflection matrix for a set of second points of this other analysis area $ZA'_{out}$ are represented here in the same manner.

These propagation images for a scatterer also show a coherent ultrasonic wave (surrounded by dashed lines) which converges, concentrates at the first point PT of the input virtual transducer $TV'_{in}$, then diverges. However, it is more difficult to discern this coherent wave because of the echoes generated by the scatterers located upstream or downstream of the focal plane, which have a reflectivity comparable with that of the virtual source analyzed.

In addition, and conversely to the previous definition of the propagation images, it is also possible to construct one or more propagation images between a plurality of input virtual transducers $TV_{in}$ (first points P1) and an output virtual transducer $TV_{out}$ (second points P2). Thus, the propagation image(s) are constructed from the focused reflection matrix $RFoc(r_{in}, r_{out}, δt)$, this or these propagation images being determined for one or more values of the additional delay δt, for one output virtual transducers $TV_{out}$ (second point P2) and for a plurality of input virtual transducers $TV_{in}$ (first points P1), the input virtual transducers $TV_{in}$ being located at spatial positions $r_{in}$ around the output virtual transducer $TV_{out}$ of spatial position $r_{out}$.

The definitions of the propagation images with respect to the input and output transducers are in fact reversed. Due to the reciprocity of the wave propagation, the images produced are very similar and the various calculations and determinations carried out from these propagation images and explained below can be carried out in a similar manner. For simplicity, the present detailed description will only explain the first direction between an input transducer and a plurality of output virtual transducers. However, it will be understood that in each of the definitions appearing in this document, it is possible to interchange the elements having the "out" index and the "in" index, and the terms "input" and "output".

In addition, it is also possible to use the two types of propagation images (in the first and second directions), and to combine them or to average these two propagation images to obtain an average propagation image that is more representative and more in contrast with the wave propagation in the medium. It is also possible to combine results coming from or determined from these two types of images, to obtain a result that is often more precise.

The focused reflection matrix $RFoc(r_{in}, r_{out}, δt)$ as defined above uses the spatial positions $r_{in}, r_{out}$ of the input virtual transducers $TV_{in}$ and output virtual transducers $TV_{out}$. These spatial positions are absolute positions within a spatial reference system. However, it is also possible to use a single absolute spatial position and a spatial position relative to this absolute spatial position. For example, we can take the absolute spatial position $r_{in}$ of the input virtual transducer and the relative spatial position $\Delta r_{out}$ of the output virtual transducer, with $\Delta r_{out} = r_{out} - r_{in}$. Conversely, we can take the absolute spatial position $r_{out}$ of the output virtual transducer and the relative spatial position $\Delta r_{in}$ of the input virtual transducer, with $\Delta r_{in} = r_{in} - r_{out}$. Each of the calculations and/ or determinations in this description can be carried out using either of the preceding definitions, or any other similar and/or equivalent definition.

Coherent Wave Extraction

The method for ultrasonic characterization implemented by the calculation unit 42 of the system 40 can be supplemented by applying a combination step in which a linear combination of a set of propagation films is carried out, each propagation film of the set being captured between a selected input virtual transducer $TV_{in}$ of a different spatial position $r_{in}$, and output virtual transducers $TV_{out}$ of spatial position $r_{out}$ such that $r_{out}=\Delta r_{out}+r_{in}$, with $\Delta r_{out}$ being predefined and identical for all propagation films of the set, and the selected input virtual transducers being close to each other.

In other words, a set of neighboring spatial positions of selected input virtual transducers $TV_{in}$ is selected, this set of spatial positions forming an area of interest for correlation, more simply called the spatial correlation area ZC, and making it possible to correlate the propagation films of these input virtual transducers. This spatial correlation area is for example a rectangular area around a reference point. It can also be the image as a whole, or any area that is or is not symmetrical in shape. The neighboring spatial positions are for example spatial positions close to one another.

By this combination of a set of several propagation films, an improved coherent wave propagation film is obtained that is improved for example in terms of coherence and contrast. The images of this new propagation film, called a coherent wave propagation film, are obtained for the same additional delays δt and for the same relative positions $\Delta r_{out}$.

This new coherent wave propagation film can then be associated with a reference input virtual transducer $TV_{in,ref}$ of spatial position $r_{in,ref}$ which represents the selected input virtual transducers from the set of propagation films (the input virtual transducers of the spatial correlation area).

According to a first example, the reference input virtual transducer $TV_{in,ref}$ is an input virtual transducer at a spatial position corresponding to the average of the spatial positions of the selected input virtual transducers. Thus, in this above variant, it is possible to express the spatial position of the reference input virtual transducer by:

$$r_{in,ref} = \frac{1}{N_{in}} \sum_{\overline{r_{in}}} \overline{r_{in}} \quad \text{(Eq. 5)}$$

$\overline{r_{in}}$ being the input virtual transducers selected,
$N_{\overline{in}}$ being the number of selected input virtual transducers composing the spatial correlation area.

According to another example, the reference input virtual transducer $TV_{in,ref}$ is an input virtual transducer at a spatial position corresponding to a weighted average of the spatial positions of the selected input virtual transducers, said weight being for example based on the reflectivity value of each point of the selected input virtual transducers. Thus, in this variant, the spatial position of the reference input virtual transducer can be expressed by:

$$r_{in,ref} = \frac{\sum_{\overline{r_{in}}} \overline{r_{in}} \cdot |RFoc(\overline{r_{in}} = \overline{r_{out}}, \delta t = 0)|}{\sum_{\overline{r_{in}}} |RFoc(\overline{r_{in}} = \overline{r_{out}}, \delta t = 0)|} \quad \text{(Eq. 6)}$$

For example, this linear combination is determined or carried out by singular value decomposition, denoted SVD, during which the singular value decomposition of the set of propagation films is calculated in order to obtain a singular vector $V_1$ associated with the singular value of greatest absolute value, this singular vector $V_1$ then being the coherent wave propagation film associated with said reference input virtual transducer $TV_{in,ref}$ and for the same additional delays δt.

The plurality of propagation films of the set is here processed by singular value decomposition in order to combine several films, meaning several acoustic disorder measurements or experiments in a region close to an input virtual transducer, which makes it possible to improve the contrast of the propagation film, and thus advantageously improve its use.

To perform this singular value decomposition calculation (in particular because the current conventional singular value decomposition tools work with two-dimensional matrices), it is possible to construct a concatenated focused reflection matrix RFoc' in which the rows of this concatenated focused reflection matrix RFoc' are the selected indices of the input virtual transducer $TV_{in}$ of spatial position $r_{in}$, and the columns of this concatenated focused reflection matrix RFoc' are the concatenated propagation films $\{\Delta r_{out}, \delta t\}$ (set of images) for each selected input virtual transducer $TV_{in}$, these propagation films being obtained for the same temporal succession of additional delays δt. This concatenated focused reflection matrix is thus the focused reflection matrix RFoc refocused on the focusing point at input $r_{in}$.

For example, this concatenated focused reflection matrix RFoc' is written:

$$RFoc'=[RFoc(r_{in},\{\Delta r_{out},\delta t\})]=[RFoc(r_{in},\{r_{in}+\Delta r_{out},\delta t\})]$$

This step of singular value decomposition SVD then provides a singular vector $V_1$ which maximizes the correlations between each of the sources of the selected input virtual transducers $TV_{in}$. The singular vector $V_1$ is associated with the singular value of greatest absolute value from the singular value decomposition. The singular vector $V_1$ is then the coherent wave propagation film associated with a reference input virtual transducer $TV_{in,ref}$ and for the same additional delays δt.

The use of singular value decomposition SVD therefore makes it possible to combine several wave propagation films while avoiding the random reflectivity introduced by speckle-type conditions. As the coherent wave is an element common to each of the propagation films, it emerges during the combination process, while the contributions of the scatterers located outside each input virtual transducer $TV_{in}$ are erased by destructive interference. This amounts to applying filtering to the propagation films, to extract the coherent wave.

Figure 7:
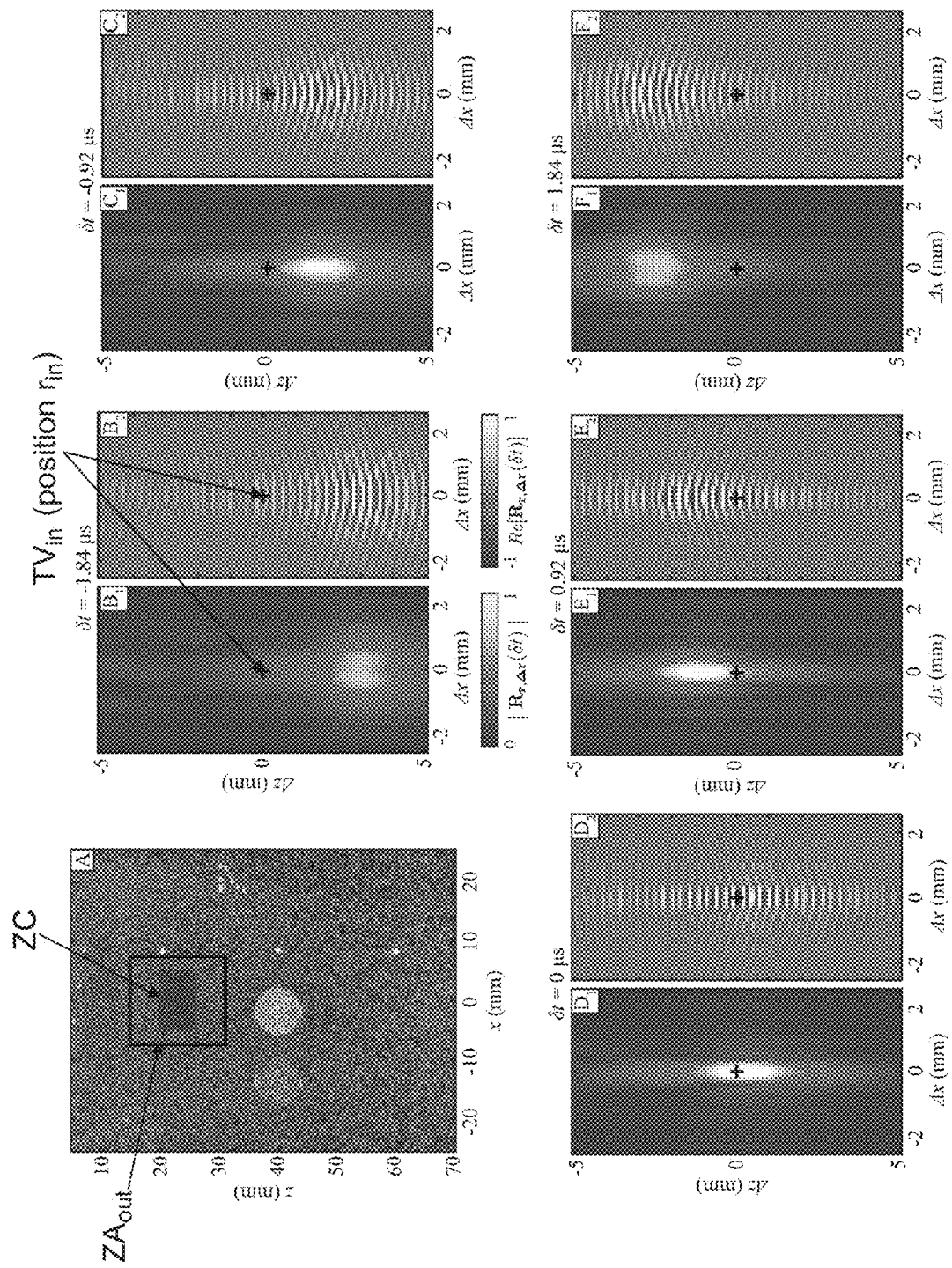
FIG. 7 shows an ultrasound image in which a set of positions associated with sub-resolution scatterers of comparable reflectivity are selected and coherent wave propagation images resulting from a combination of the propagation images associated with each selected position are obtained for several additional delays.

The image denoted A in FIG. 7 shows the same ultrasound image as those in FIGS. 5 and 6. In this figure, an example is considered of an analysis area $ZA_{out}$ associated with an input virtual transducer selected from the set of selected input virtual transducers $TV_{in}$, these selected virtual transducers being represented in this image A by a grid of points of rectangular shape. The points of this grid represent the set of the selected input virtual transducers $TV_{in}$, called the coherence area ZC (i.e. the neighboring selected input virtual transducers), for performing the coherent combination of the propagation films.

The images denoted B to F of FIG. 7 are coherent wave propagation images of the analysis area $ZA_{out}$ of image A of FIG. 7 for several additional delay values δt which represent the first singular vector $V_1$. The same representation of the first image being amplitude and of the second image being the real part is used in this example as was presented for the previous figures.

The images in FIG. 7 show that the coherent part of the ultrasonic wave can also be extracted for a set of first points P1 (input virtual transducer $TV_{in}$) located in the speckle. In fact, in these images, a single coherent wave is observed which moves from the bottom to the top while concentrating at the position of the input virtual transducer $TV_{in}$, while the propagation images not processed by the singular value decomposition process SVD of this experiment would resemble those presented in the images denoted B to F in FIG. 6.

Singular value decomposition makes it possible to extract the coherent wave from the propagation images/films in a very reliable manner. For example, in FIG. 8A, the first curve A1 corresponds to the amplitude of the signal at the confocal point as a function of the additional delay δt (here between −3 μs and +3 μs) for one of the propagation films obtained for an input virtual transducer $TV_{in}$ belonging to the coherence area ZC. The confocal point is the point of the propagation images defined by $\Delta x=\Delta z=|\Delta r|=0$ ($r_{in}=r_{out}$) represented in our example by the x located at the center of each propagation image and which corresponds to the position of the input virtual transducer. This curve A1 is very chaotic in the case represented, because the confocal position r coincides with a "speckle" type area. The coherent wave is then entirely or partially hidden by the echoes coming from scatterers located upstream or downstream of this confocal area. In this figure, curve A2 corresponds to the amplitude of the signal of the coherent wave propagation film (first singular vector $V_1$) resulting from singular value decomposition of the preceding propagation film, and for the same confocal point. This curve A2 shows a single peak centered at zero additional delay δt, which demonstrates good focusing of the wave even for this specific case involving a poorly reflecting element.

Figure 8A:
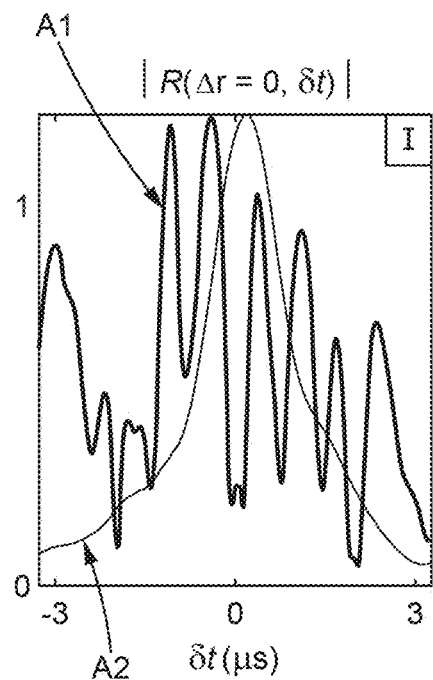
FIG. 8A shows curves of temporal variations of the intensity of the central point of a propagation image associated with a position corresponding to sub-resolution scatterers of comparable reflectivity and of the coherent wave propagation image.
Figure 8B:
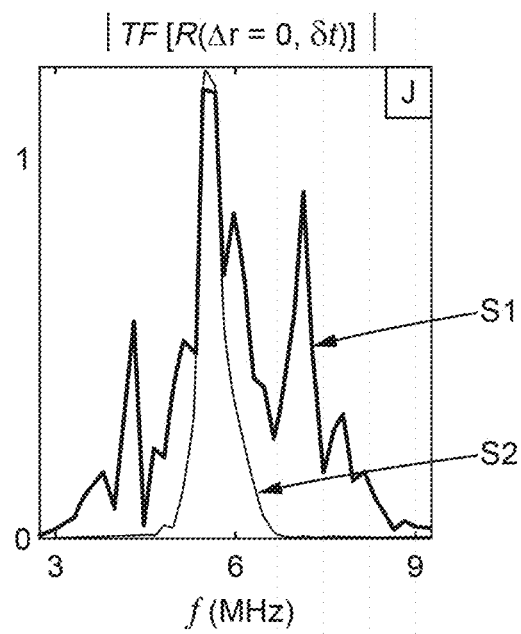
FIG. 8B shows frequency spectra of the curves of FIG. 8A.

FIG. 8B shows the frequency spectra of the signals of FIG. 8A, curve S1 corresponding to the frequency spectrum of the signal of curve A1, and curve S2 corresponding to the frequency spectrum of the signal of curve A2. A loss of temporal resolution of the coherent wave (visible in FIG. 7) is nevertheless observed, which results in a reduction in the spectral width of the signals studied. If necessary, this phenomenon can be corrected by applying a spectrum equalization step.

The coherent wave propagation images are analogous to the propagation images associated with an echogenic scatterer but of reduced spectral width.

These curves A2, S2 illustrate the efficiency of the combination/singular value decomposition step for extracting or filtering coherent wave propagation films with a single peak (a single main wave).

Coherent Wave in a Ballistic Reference System

The calculation of the focused reflection matrix $RFoc(r_{in}, r_{out}, δt)$ assumes a model of the speed of the ultrasonic waves in the medium (for example, a constant speed of sound $c_0$). Indeed, the outward times-of-flight $\tau_{in}$ and the return times-of-flight $\tau_{out}$ of the wave are conventionally calculated with geometric formulas for calculating the distance between the transducers 11 and each point in the medium, and with this assumption of constant speed of sound.

Therefore, the propagation images, propagation films, and coherent wave propagation films calculated above include this assumption of a constant speed of sound $c_0$. In these images and films, the coherent wave results from a process of digital time reversal based on the assumed speed of sound model. This wave therefore propagates at the assumed speed of sound $c_0$. At time δt=0, it is located at the depth of the input virtual transducer $TV_{in}$ (the central x in these figures), meaning for Δz=0. The time-of-flight of the coherent wave therefore follows the following ballistic propagation relation:

$$\delta t(\Delta r_{out})=-\text{sign}(\Delta z_{out})\cdot|\Delta r_{out}|/c_0 \quad (Eq. 7)$$

where:
$c_0$ is the speed of sound in the medium,
$|\Delta r_{out}|$ is the modulus of the vector between the input virtual transducer $TV_{in}$ and the output virtual transducer $TV_{out}$, $\Delta r_{out}=r_{out}-r_{in}$,
δt is the additional delay,
$\Delta z_{out}$ is the component along the second axis Z of the spatial position vector $\Delta r_{out}$.

In other words, in these propagation images, the theoretical wave which propagates at the speed of sound $c_0$ forms an arc of a circle centered on the origin of the image (i.e. the input virtual transducer $TV_{in}$ of spatial position $r_{in}$). The ballistic propagation relation therefore links the relative position $\Delta r_{out}$ to the additional delay δt by the speed of sound $c_0$. The negative sign emphasizes the fact that this is a process of digital time reversal.

It is then possible to extract, from the propagation film or from the coherent wave propagation film, an image focusing on the wave within the ballistic reference system, this image being called the wavefront image and following this theoretical wave at the speed of sound $c_0$: For each propagation image or coherent wave propagation image, at an additional delay δt, we extract the values (sound pressure value) which lie on this arc of a circle (i.e. which satisfy the above ballistic propagation relation). A new image is thus constructed, called the wavefront image, which represents the evolution of the propagation film or coherent wave propagation film in the ballistic reference system. This wavefront image is therefore a wavefront image within the ballistic reference system.

According to a first variant, the wavefront image is determined indirectly by calculating a propagation film or coherent wave propagation film, and by extracting the appropriate data from this film as explained above in order to determine the wavefront image during the additional delay interval.

The method for ultrasonic characterization implemented by the calculation unit 42 of the system 40 can therefore be supplemented by applying determining a wavefront image for an input virtual transducer $TV_{in}$ or for a reference input virtual transducer $TV_{in,ref}$ and for an additional delay interval, said wavefront image being determined from:
  images of a propagation film or of a coherent wave propagation film, and
  a ballistic propagation relation of the type:
  $\delta t(\Delta r_{out})=-\text{sign}(\Delta z_{out})\cdot|\Delta r_{out}|/c_0$ which makes it possible to extract values from each of the images of the films in order to construct the wavefront image.

According to a second variant, a wavefront image is determined directly from the experimental reflection matrix $R_{ui}(t)$, by imposing the above ballistic propagation relation.

The method for ultrasonic characterization implemented by the calculation unit 42 of the system 40 can therefore be supplemented by applying determining a wavefront image for an input virtual transducer $TV_{in}$ and for an additional delay interval, said wavefront image being determined from:

the focused reflection matrix $RFoc(r_{in}, r_{out}, \delta t)$ and a ballistic propagation relation of the type $\delta t(\Delta r_{out}) = -\text{sign}(\Delta z_{out}) \cdot |\Delta r_{out}|/c_0$, which makes it possible to extract values from the focused reflection matrix in order to construct the wavefront image.

In all these variants, the wavefront image makes it possible to estimate the pressure field (response during emission-reception) generated by the input virtual transducer $TV_{in}$ or reference input virtual transducer $TV_{in,ref}$ based on the echoes measured by the transducers of the probe.

Note that the signals contained in the wavefront image is a sub-matrix of the focused reflection matrix. Therefore, for the calculations, we can restrict ourselves to signals which satisfy the above ballistic propagation relation. In this case, the wavefront image is the focused reflection matrix $RFoc(r_{in}, r_{out}, \delta t)$.

The points or pixels of these wavefront images have the spatial position $\Delta r_{out} = r_{out} - r_{in}$, meaning a position relative to the position $r_{in}$ of the input virtual transducer $TV_{in}$. The coordinates are thus denoted $\Delta x$ on the abscissa and $\Delta z$ on the ordinate on these images. These wavefront images can also be determined for a three-dimensional imaging method. Other coordinates are then used to represent wavefront images in various planes.

Figure 9A:
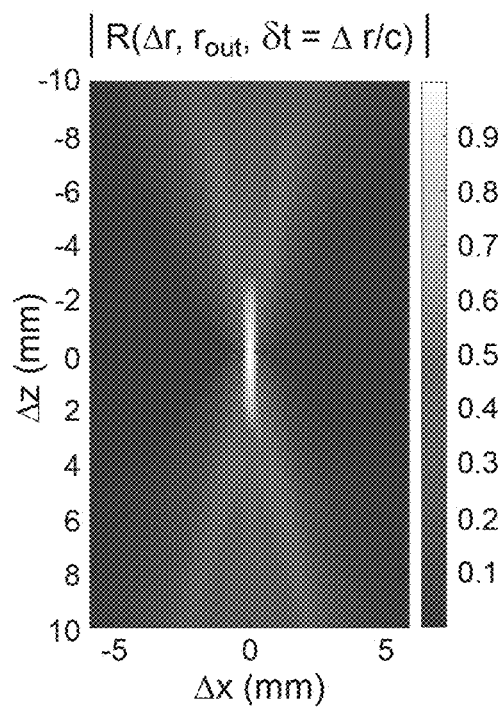
FIG. 9A shows the image amplitude of the wavefront associated with the same position as that of FIG. 5.
Figure 9B:
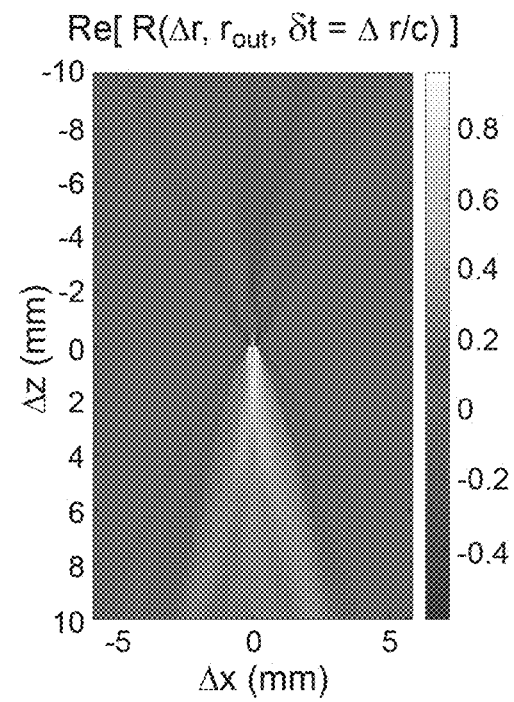
FIG. 9B shows the real part of the same wavefront image as that used in FIG. 9A.

FIG. 9A shows the amplitude of such a wavefront image, and FIG. 9B shows the real part of this wavefront image. In FIG. 9B, note a phase shift of $\pi$ radians at the passage through the focusing point of the input virtual transducer $TV_{in}$ (spatial position $r_{in}$ of coordinates $\Delta x = \Delta z = 0$ in this figure). This phase shift is known as the Gouy phase shift. The wavefront image clearly illustrates this phenomenon.

As is true with propagation images, it is possible to reverse the role played by the input virtual transducers $TV_{in}$ and the output virtual transducers $TV_{out}$. In this case, an estimate of the pressure field generated by the focusing is obtained as output.

Determination of the Integrated Speed of Sound

The method and system for ultrasonic characterization of a medium according to this disclosure and implemented by the calculation unit 42 of the system 40 is also able to determine the integrated speed of sound at a point in the medium. The integrated speed of sound is an estimate of the average value of the speed of sound between the transducers of the probing device 41 and a point of the medium. More precisely, this integrated speed of sound integrates all the local speeds of sound of the areas crossed by the outward and then the return path of the ultrasonic wave.

In this case, the method comprises:

determining a wavefront image for an input virtual transducer $TV_{in}$ and for an additional delay interval, said wavefront image being determined as described above as a function of a speed of sound $c_0$ in the medium, determining a depthwise position $\Delta z^{(0)}$ of the center of the focal spot in the wavefront image for the input virtual transducer $TV_{in}$, and calculating an integrated speed of sound $c^{(1)}$ based on the following formula:

$$c^{(1)}(r_{in}) = c_0 \sqrt{1 + \frac{\Delta z^{(0)}(r_{in})}{z_{in}}} \quad \text{(Eq. 8)}$$

where $z_{in}$ is the component along a second axis Z of the spatial position vector $r_{in}$ of the input virtual transducer $TV_{in}$.

"Center of the focal spot in the wavefront image" is understood to mean, in one example, the position of the maximum of the focal spot in the wavefront image; meaning the position of the pixel having the greatest value in the entire wavefront image. It should be noted that only one focal spot can be observed in the wavefront image, and its position is therefore unique. Thus, the position of the center of the focal spot is also unique, and represents the depthwise position $\Delta z^{(0)}(r_{in})$ to be used to correct the speed of sound $c_0$, for the point in the medium corresponding to the spatial position $r_{in}$ of the input virtual transducer $TV_{in}$.

For example, the center of the focal spot is determined by searching the wavefront image for the spatial position of the point of greatest value, and the depthwise position $\Delta z^{(0)}$ of the center of the focal spot is then the component in the direction of the depth axis Z, corresponding to axis $\Delta z$, of this point of greatest value.

Note that the depthwise position $\Delta z^{(0)}$ is determined for each input virtual transducer $TV_{in}$ taken in the medium or conversely for each output virtual transducer $TV_{out}$ taken in the medium. More generally, this depthwise position depends on each considered point of spatial position r and can be denoted $\Delta z^{(0)}(r)$ with $r = r_{in}$ or $r = r_{out}$.

Indeed, in the images of the propagation film or of the coherent wave propagation film, the ultrasonic wave is focused at the moment of zero additional delay $\delta t$ ($\delta t = 0$) only if the speed of sound $c_0$, used for calculating the focused reflection matrix $RFoc(r_{in}, r_{out}, \delta t)$ through calculations of the outward time-of-flight and return time-of-flight, and for calculating the wavefront image through the ballistic propagation relation, is a speed of sound value which corresponds to an integrated speed of sound that is correct for the actual medium between the transducers 11 of the probing device 41 and the point of the medium corresponding to the input virtual transducer $TV_{in}$ of spatial position $r_{in}$.

Figure 10:
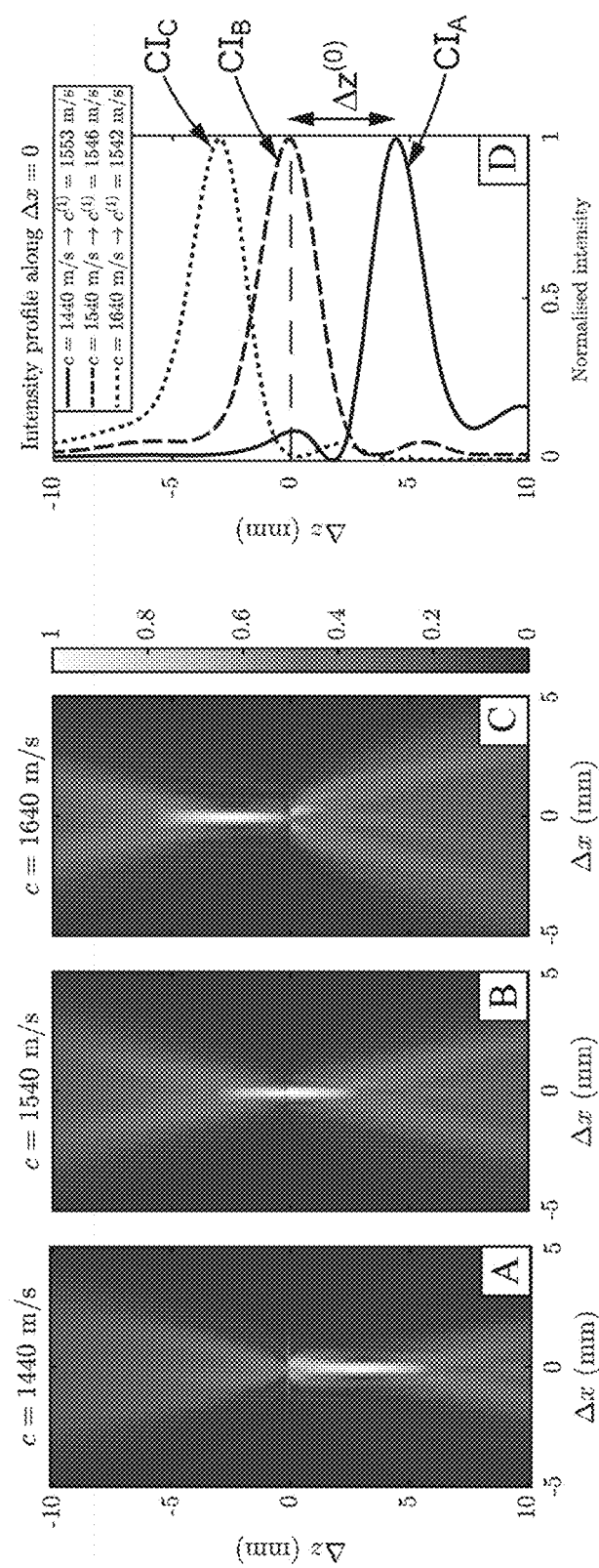
FIG. 10 shows the amplitude of several wavefront images associated with the same position as that selected for FIG. 5 and obtained for three assumed speeds of sound, and intensity curves on the ordinate axis $\Delta z$ of these wavefront images.

For example, FIG. 10 illustrates this process. In this FIG. 10, the images denoted A, B, and C show wavefront images obtained with predefined speeds of sound $c_0$ of 1440 m/s, 1540 m/s, and 1640 m/s respectively. In these wavefront images, we observe a focal spot which moves along the ordinate axis $\Delta z$, meaning depthwise (direction Z). The graph denoted D then shows the three intensity curves $CI_A$, $CI_B$ and $CI_C$ of these wavefront images on this ordinate axis $\Delta z$, meaning the axis for which $\Delta x = 0$.

For example, the depthwise position $\Delta z^{(0)}(r_{in})$ of the focal spot is obtained as illustrated in FIG. 10, i.e. by determining the depthwise position of the maximum of the values of the wavefront image on the ordinate axis $\Delta z$, such that $\Delta x = 0$. The depthwise position $\Delta z^{(0)}(r_{in})$ of the focal spot in the wavefront image is obtained by searching the wavefront image for the position on the ordinate axis $\Delta z$ having a maximum value in this wavefront image, this ordinate axis $\Delta z$ corresponding to a zero $\Delta x$ abscissa in the wavefront image.

For example, for the intensity curve $CI_A$ of graph D, the depthwise position $\Delta z^{(0)}(r_{in})$ is substantially equal to 4.5 mm, which will result in an estimate of the integrated speed of sound $c^{(1)}(r_{in})$ that is greater than the speed of sound initially assumed $c^{(0)}$, at the position $r_{in}$ of the selected input virtual transducer $TV_{in}$, such that the vertical position along the $\Delta z$ axis of the focal spot of image A will be moved upwards and therefore towards the point of origin ($\Delta x = \Delta z = 0$) of the input virtual transducer, which corresponds to an adjustment by calculating the integrated speed of sound for this point in the medium of the input virtual transducer $TV_{in}$.

Consequently, in practice, it is possible to be satisfied with calculating the values of the wavefront image on the $\Delta z$ axis, for which $\Delta x=0$, to determine a speed of sound or integrated speed of sound.

The method for ultrasonic characterization of a medium thus comprises the following steps to determine an integrated speed of sound:

generating a series of incident ultrasonic waves $US_{in}$ in an area of said medium, by means of an array 10 of transducers 11, said series of incident ultrasonic waves being an emission basis i; and generating an experimental reflection matrix $R_{ui}(t)$ defined between the emission basis i as input and a reception basis u as output;

determining a focused reflection matrix $RFoc(r_{in}, r_{out}, \delta t)$ which comprises responses of the medium between an input virtual transducer $TV_{in}$ of spatial position $r_{in}$ and an output virtual transducer $TV_{out}$ of spatial position $r_{out}$, the responses of the output virtual transducer $TV_{out}$ being obtained at a time instant that is shifted by an additional delay $\delta t$ relative to the time instant of the responses of the input virtual transducer $TV_{in}$, determining a wavefront image for the input virtual transducer $TV_{in}$ and for an additional delay interval, said wavefront image being determined as a function of the speed of sound $c_0$ in the medium, and said wavefront image being determined based on:

the focused reflection matrix $RFoc(r_{in}, r_{out}, \delta t)$ and a ballistic propagation relation of the type $\delta t(\Delta r_{out})=-\text{sign}(\Delta z_{out})\cdot|\Delta r_{out}|/c_0$, which makes it possible to extract values from the focused reflection matrix to construct the wavefront image, and in which:

$\delta t$ is the additional delay, $|\Delta r_{out}|$ is the modulus of the vector between the input virtual transducer $TV_{in}$ and the output virtual transducer $TV_{out}$, with $\Delta r_{out}=r_{out}-r_{in}$, $\Delta z_{out}$ is the component along a depth axis Z of the spatial position vector $\Delta r_{out}$, determining a depthwise position $\Delta z^{(0)}$ of the center of the focal spot in the wavefront image, and calculating an integrated speed of sound $c^{(1)}$, from the following formula:

$$c^{(1)}(r_{in}) = c_0 \sqrt{1 + \frac{\Delta z^{(0)}(r_{in})}{z_{in}}} \quad \text{(Eq. 9)}$$

where $z_{in}$ is the component along the depth axis Z of the spatial position vector $r_{in}$ of the input virtual transducer $TV_{in}$.

Optionally, this method can be iterated one or more times as defined above, by calculating a new integrated speed of sound $c^{(n+1)}$ based on the determination of a wavefront image obtained with the previous integrated speed of sound $c^{(n)}$, the determination of a depthwise position $\Delta z^{(n)}$ of the center of the focal spot, and the calculation of the new integrated speed of sound $c^{(n)}$ by the same iteration formula:

$$c^{(n+1)}(r_{in}) = c^{(n)}(r_{in}) \sqrt{1 + \frac{\Delta z^{(0)}(r_{in})}{z_{in}}} \quad \text{(Eq. 10)}$$

In practice, this iterative process converges extremely quickly to an optimum integrated speed of sound which corresponds to the best integrated speed of sound for the transducers 11 of the probing device and the chosen point in the medium (input virtual transducer).

Furthermore, alternatively, this method for determining the integrated speed of sound can be improved by performing, between determining a wavefront image and determining the depthwise position $\Delta z^{(0)}(r_{in})$ of a focal spot, improving the wavefront image in which a linear combination of a set of wavefront images corresponding to a given coherence area ZC is carried out, each wavefront image of the set being obtained between a selected input virtual transducer $TV_{in}$ of a different spatial position $r_{in}$, and output virtual transducers $TV_{out}$ of spatial position $r_{out}$ such that $r_{out}=\Delta r_{out}+r_{in}$, with $\Delta r_{out}$ being predefined and identical for all wavefront images of the set, and the selected input virtual transducers being close to each other. An improved wavefront image or coherent wavefront image associated with a reference input virtual transducer $TV_{in,ref}$ is thus obtained, this reference input virtual transducer $TV_{in,ref}$ representing the input virtual transducers of the set of wavefront images used and associated with the chosen coherence area ZC, and for the same relative positions $\Delta r_{out}$.

For example, the reference input virtual transducer $TV_{in,ref}$ is an input virtual transducer of a spatial position corresponding to the average of the spatial positions of the selected input virtual transducers or a weighted average of the spatial positions of the selected input virtual transducers, as already explained above for the case of propagation films.

In summary, in the method of this disclosure, the following steps are added:

between determining a wavefront image and determining the depthwise position $\Delta z^{(0)}(r_{in})$ of a focal spot, improving the wavefront image is performed in which a linear combination of a set of wavefront images corresponding to a coherence area is carried out, each wavefront image being obtained between a selected input virtual transducer ($TV_{in}$) of different spatial position $r_{in}$, and output virtual transducers ($TV_{out}$) of spatial position $r_{out}$ such that $r_{out}=\Delta r_{out}+r_{in}$, with $\Delta r_{out}$ being predefined and identical for all wavefront images of the set, and the selected input virtual transducers being close to each other, in order to obtain an improved wavefront image associated with a reference input virtual transducer ($TV_{in,ref}$), this reference input virtual transducer $TV_{in,ref}$ being characteristic of the input virtual transducers of the set of wavefront images used and associated with the coherence area ZC, and in determining a depthwise position $\Delta z^{(0)}(r_{in})$, the improved wavefront image is used instead of the wavefront image, the depthwise position of the center of the focal spot is relative to the spatial position of the reference input virtual transducer $TV_{in,ref}$, and this depthwise position of the center of the focal spot makes it possible to estimate an integrated speed of sound $c^{(1)}(r_{in,ref})$ at the spatial position of the reference input virtual transducer $TV_{in,ref}$.

The improved wavefront image (coherent wavefront image) is then used (instead of the wavefront image) to determine the axial position of the center of the focal spot. This distance or depthwise position $\Delta z^{(0)}(r_{in,ref})$ is then characteristic of an incorrect model for the speed of sound and can be used to estimate the integrated speed of sound $c^{(1)}(r_{in,ref})$ associated with the spatial position $r_{in,ref}$ of the reference input virtual transducer $TV_{in,ref}$.

According to one embodiment, the linear combination is determined by calculating the singular value decomposition SVD of the set of wavefront images in order to obtain a singular vector $W_1$ associated with the singular value of greatest absolute value of the singular value decomposition, this singular vector $W_1$ then being the improved wavefront image corresponding to said reference input virtual transducer $TV_{in,ref}$ and for the same additional delays $\delta t$.

The plurality of wavefront images of the set can here be processed by singular value decomposition in order to combine several acoustic disorder measurements or experiments in a region close to an input virtual transducer, which makes it possible to avoid fluctuations linked to disorder and improve the contrast of the wavefront image as well as its use.

In addition, it is possible to determine an optimum speed of sound of the medium (realistic for the medium as a whole) by calculating an integrated speed of sound as described above, and by using, for the linear combination of the set of wavefront images, a set of wavefront images corresponding to selected input virtual transducers ($TV_{in}$) which substantially cover the entire area of interest in the medium. In particular, these selected input virtual transducers can be regularly distributed over the entire area of interest of the medium, with a predetermined spacing. For example, these selected input virtual transducers may represent 20% or more of the number of input virtual transducers used for example to construct an ultrasound image of the medium covering the area to be studied.

Note that the depthwise distances or positions $\Delta z^{(0)}(r_{in})$ or $\Delta z^{(0)}(r_{in,ref})$ can be interpreted as a focusing error at output due to the aberrations undergone during backpropagation of echoes coming from spatial positions $r_{in}$ or $r_{in,ref}$. The integrated speed of sound measurement can also be determined by probing the aberrations undergone by the wavefronts during the outward path. This measurement is described by reversing the "in" and "out" indications in the above equations while reversing the role of the input and output virtual transducers, to obtain another estimate of the integrated speed of sound $c^{(1)}_{out}$.

In addition, it is possible to improve the estimate of the integrated speed of sound by combining the measurements or estimates of the integrated speed of sound that are obtained from the aberrations generated on the outward and/or return journey, i.e. the integrated speeds of sound $c^{(1)}_{in}$ and $c^{(1)}_{out}$.

The method is then supplemented by the following operations:
- the roles of the input virtual transducer(s) and of the output virtual transducer(s) are reversed in order to determine an integrated speed of sound $c^{(1)}(r_{out})$ with respect to an output virtual transducer, and
- the integrated speed of sound $c^{(1)}(r_{in})$ with reference to the input virtual transducer and the integrated speed of sound $c^{(1)}(r_{out})$ with reference to the output virtual transducer are combined to obtain an improved integrated speed of sound.

Integrated Speed of Sound Images

The method for ultrasonic characterization implemented by the calculation unit 42 of the system 40 can be supplemented by constructing one or more integrated speed of sound images, this or these integrated speed of sound images being determined by at least one calculation of an integrated speed of sound as described above and for a plurality of points in the medium corresponding to input virtual transducers $TV_{in}$ (first points P1) of spatial position $r_{in}$.

Figure 11:
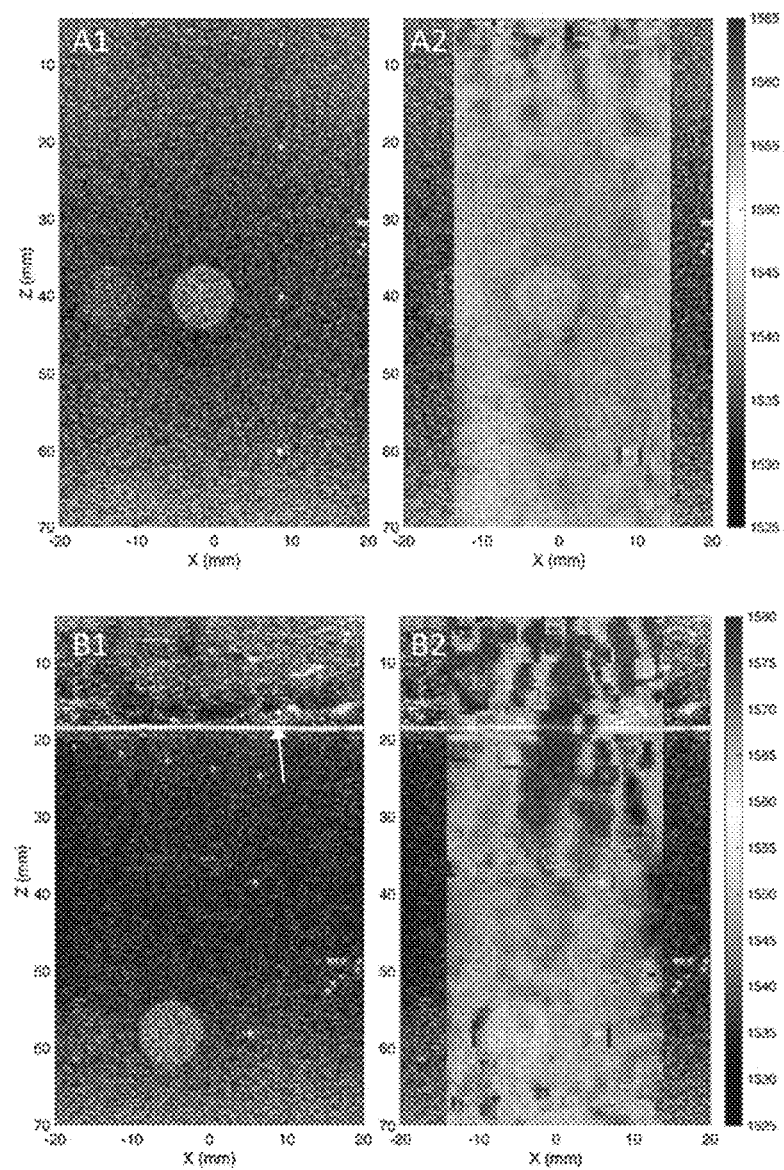
FIG. 11 shows ultrasound images and corresponding images of the integrated speed of sound.

FIG. 11 illustrates two examples of such images.

In the first example, corresponding to images A1 and A2 of FIG. 11, the medium is of the phantom type with a reference speed of sound given for substantially $c_{ref}$=1542 m/s. Image A1 is the standard ultrasound image, while image A2 is the integrated speed of sound image obtained by the above method. This integrated sound image A2 allows estimating an average value for the speed of sound of 1544 m/s in the medium with a standard deviation of 20+/−3 m/s, which is entirely in agreement with the reference value of the speed of sound for this medium.

In the second example, corresponding to images B1 and B2 of FIG. 11, the medium is a layered medium with a first layer almost 20 mm thick, having a fibrous structure and a speed of sound of approximately 1570 m/s, positioned on the same phantom-type medium having a speed of sound, predetermined by construction, of substantially 1542 m/s. Image B1 is the standard ultrasound image of this medium, while image B2 is the integrated speed of sound image obtained by the method disclosed above. This integrated sound image B2 reflects a higher speed of sound in the first layer of about 1580 m/s and a lower speed of sound that is below but not identical to that of the expected speed of sound and corresponding to that of this medium studied in the first example. This effect is due to the fact that the speed of sound calculated by the method is an integrated speed of sound which corresponds to an average or integrated speed of sound over the entire outward and return path of the waves between the transducers 11 and the point of the medium.

Correction of Axial Aberrations

The method and system for ultrasonic characterization of a medium according to this disclosure and implemented by the calculation unit 42 of the system 40 is also able to determine an axial correction.

The method for ultrasonic characterization of a medium in order to determine a temporal and local characterization of an ultrasonic focusing with an axial correction comprises the following steps, already explained, for obtaining a focused reflection matrix:

- generating a series of incident ultrasonic waves $US_{in}$ in an area of said medium, by means of an array 10 of transducers 11, said series of incident ultrasonic waves being an emission basis i; and
- generating an experimental reflection matrix $R_{ui}(t)$ defined between the emission basis i as input and a reception basis u as output;
- determining a focused reflection matrix $RFoc(r_{in}, r_{out}, \delta t)$ which comprises responses of the medium between an input virtual transducer $TV_{in}$ of spatial position $r_{in}$ and an output virtual transducer $TV_{out}$ of spatial position $r_{out}$, the responses of the output virtual transducer $TV_{out}$ being obtained at a time instant that is shifted by an additional delay $\delta t$ relative to a time instant of the responses of the input virtual transducer $TV_{in}$,
- determining a wavefront image for an input virtual transducer $TV_{in}$ and for an additional delay interval, said wavefront image being determined as described above as a function of a speed of sound $c_0$ in the medium, and determining a depthwise position $\Delta z^{(0)}(r_{in})$ of the center of the focal spot in the wavefront image.

"Center of the focal spot in the wavefront image" is understood to mean, in one example, the position of the maximum of the focal spot in the wavefront image; meaning the position of the pixel having the greatest value of the entire wavefront image. The center of the focal spot and the depthwise position can be found/determined according to one of the techniques already described above.

This method further comprises a step of determining a corrected focused reflection matrix $RFoc^{(1)}(r_{in}, r_{out}, \delta t)$ by translation of the responses of the focused reflection matrix $RFoc(r_{in}, r_{out}, \delta t)$ of a spatial translation in the depthwise direction Z, said spatial translation being a function of the previously determined depthwise position $\Delta z^{(0)}(r_{in})$.

According to a first variant, the spatial translation is performed by spatial translation of the axial component of the output virtual transducer $TV_{out}$ of spatial position $r_{out}$ (along the depth axis Z) with a correction value $\Delta z_{corr}(r_{in})$ equal to $2.\Delta z^{(0)}(r_{in})$, to obtain the corrected focused reflection matrix $RFoc^{(1)}(r_{in}, r_{out}, \delta t)$, such that:

$$RFoc^{(1)}(r_{in},r_{out},\delta t)=RFoc(r_{in},\{x_{out},z_{out}+\Delta z_{corr}(r_{out})\},\delta t) \quad \text{(Eq. 11)}$$

A corrected ultrasound image $I^{(1)}(r_{in})$ can then be constructed from the corrected focused reflection matrix $RFoc^{(1)}(r_{in}, r_{out}, \delta t)$ characterized by $r=r_{in}=r_{out}$ and $\delta t=0$, to obtain:

$$I^{(1)}(r)=RFoc^{(1)}(r_{in},r_{out}=r_{in},\delta t=0) \quad \text{(Eq. 12)}$$

Conversely, the spatial translation can also correspond to the spatial translation of the components along the depth axis Z of the input virtual transducer $TV_{in}$ of spatial position $r_{in}$ with a correction value $\Delta z_{corr}(r_{in})$ equal to $2.\Delta z^{(0)}(r_{in})$, to obtain the following corrected focused reflection matrix $RFoc^{(1)}(r_{in}, r_{out}, \delta t)$:

$$RFoc^{(1)}(r_{in},r_{out},\delta t)=RFoc(\{x_{in},z_{in}+\Delta z_{corr}(r_{in})\},r_{out},\delta t) \quad \text{(Eq. 13)}$$

Note that the depth wise position $\Delta z^{(0)}$ is determined for each input virtual transducer $TV_{in}$ taken in the medium and is characteristic of the aberration undergone during the return journey. By reversing the "in" and "out" notations, it is possible to determine the position $\Delta z^{(0)}(r_{out})$ characteristic of the aberration undergone during the outward journey, for each output virtual transducer $TV_{out}$ taken in the medium. In other words, more generally, this depthwise position depends on each considered point of spatial position r and can also be denoted $\Delta z^{(0)}=\Delta z^{(0)}(r)$ with $r=r_{in}$ or $r=r_{out}$.

According to a second variant, the spatial translation is performed by:
  calculating a correction value $\Delta z_{corr}(r)$ equal to $\Delta z^{(1)}(r)$ which is determined by the following formula:

$$\Delta z^{(1)}(r) = z^{(1)}(r) - z_{in} \quad \text{(Eq. 14)}$$

with $$z^{(1)}(r) = z\sqrt{1 + \frac{\Delta z^{(0)}(r_{in})}{z_{in}}}$$

where this equation is applied for
$r=r_{in}$ and $r=r_{out}$
$z=z_{in}$ and $z=z_{out}$ is the component along a depth axis Z of the spatial position $r_{in}$ of the input virtual transducer $TV_{in}$ or of the spatial position $r_{out}$ of the output virtual transducer $TV_{out}$,
  calculating the corrected focused reflection matrix $RFoc^{(1)}(r_{in}, r_{out}, \delta t)$ by spatial translation of the components along the depth axis Z of the input virtual transducer $TV_{in}$ of spatial position $r_{in}$ of said correction value $\Delta z_{corr}(r_{in})$ and of the output virtual transducer $TV_{out}$ of spatial position $r_{out}$ of said correction value $\Delta z_{corr}(r_{out})$, such that:

$$RFoc^{(1)}(r_{in},r_{out},\delta t)=RFoc(\{x_{in},z_{in}+\Delta z_{corr}(r_{in})\},\{x_{out},z_{out}+\Delta z_{corr}(r_{out})\},\delta t)$$

This calculation can also be expressed as a function of the integrated speed of sound $c^{(1)}(r)$ based on the following formula:

$$c^{(1)}(r_{in}) = c_0\sqrt{1 + \frac{\Delta z^{(0)}(r_{in})}{z_{in}}} \quad \text{(Eq. 15)}$$

where $z_{in}$ is the component along a second axis Z of the spatial position vector $r_{in}$ of the input virtual transducer $TV_{in}$, and
the translation calculation $\Delta z^{(1)}(r)$ by:

$$\Delta z^{(1)}(r) = z^{(1)}(r) - z_{in} \quad \text{(Eq. 16)}$$

with $$z^{(1)}(r) = z_{in}\frac{c^{(1)}(r)}{c_0} = z_{in}\sqrt{1 + \frac{\Delta z^{(0)}(r_{in})}{z_{in}}}$$

According to some modifications to the two preceding variants, the translations can be implemented by calculating a spatial Fourier transform, phase shifting by a phase ramp where the slope depends on the correction value, then a spatial inverse Fourier transform. This implementation has the advantage of making it possible to combine translation and interpolation for new spatial coordinates.

As an example, the method thus implemented carries out:
  determining a spatial frequency matrix $RFreq_z(r_{in}, r_{out}, k_{zout}, \delta t)$ which is a spatial Fourier transform in a depthwise direction of the focused reflection matrix $RFoc(r_{in}, r_{out}, \delta t)$, according to the equation:

$$RFreq_z(r_{in},x_{out},k_{zout},\delta t)TF_{zout}[RFoc(r_{in},r_{out},\delta t)] \quad \text{(Eq. 17)}$$

where
  $TF_{zout}$ is the spatial Fourier transform in the depthwise direction $\Delta z_{out}$,
  $k_{zout}$ is the corresponding wave number comprised within the interval $[\omega^-/c_0, \omega^+/c_0]$, with pulses $\omega^-$ and $\omega^+$ which are the pulses bounding the bandwidth of the ultrasonic waves, and
  $x_{out}$ is the transverse component in the direction of the X axis, of each output virtual transducer $TV_{out}$ of spatial position $r_{out}$, and
  determining a corrected focused reflection matrix $RFoc^{(1)}(r_{in}, r_{out}, \delta t)$ corresponding to the inverse spatial Fourier transform in the same depthwise direction, of the product of the spatial frequency matrix $RFreq_z(r_{in}, x_{out}, k_{zout}, \delta t)$ by phase ramp of the depthwise correction value $\Delta z_{corr}$, i.e. equal to $2.\Delta z^{(0)}(r_{in})$ according to the above variants, and determined for each spatial position of the input virtual transducer $TV_{in}$, and in which the following formula is applied:

$$RFoc^{(1)}(r_{in},r_{out},\delta t)=TF_{kz_{out}}^{-1}[RFreq_z(r_{in},x_{out},k_{z,out},\delta t)e^{-ik_{z,out}\Delta z_{corr}}] \quad \text{(Eq. 18)}$$

where
  $e^{-ix}$ is the complex exponential function,
  $\Delta z_{corr}$ is the correction value determined by the depthwise position of the center of the focal spot in the wavefront image.

The spatial Fourier transform in direction $\Delta z_{out}$ can for example be described by the following spatial discrete Fourier transform formula:

$$RFreq_z(r_{in}, x_{out}, k_{z,out}, \delta t) = \qquad (Eq. 19)$$
$$TF_{z_{out}}[RFoc(r_{in}, r_{out}, \delta t)] = \sum_{\Delta z_{out}} RFoc(r_{in}, r_{out}, \delta t) e^{-ik_{z,out} \cdot \Delta z_{out}}$$

Other formulations of the Fourier transform and spatial Fourier transform exist.

The inverse spatial Fourier transform in direction $\Delta z_{out}$ can then be explained by the following reciprocal formula:

$$RFoc^{(1)}(r_{in}, r_{out}, \delta t) = \qquad (Eq. 20)$$
$$TF_{k_{z_{out}}}^{-1}\left[RFreq_z(r_{in}, x_{out}, k_{z,out}, \delta t) e^{-ik_{z,out} \Delta z_{corr}}\right] =$$
$$\sum_{k_{z,out}} RFreq_z(r_{in}, x_{out}, k_{z,out}, \delta t) e^{-ik_{z,out} \Delta z_{corr}} e^{ik_{z,out} \Delta z_{out}}$$

According to a third variant, the responses are axially translated by calculating or determining a corrected focused reflection matrix $RFoc^{(1)}(r_{in}, r_{out}, \delta t)$ with a new speed of sound $c_1(r)$ which replaces the assumed speed of sound $c_0$.

The method of this third variant thus further comprises the following steps to obtain an axially corrected focused reflection matrix:

calculating an integrated speed of sound $c^{(1)}(r)$ from the following formula:

$$c^{(1)}(r_{in}) = c_0 \sqrt{1 + \frac{\Delta z^{(0)}(r_{in})}{z_{in}}} \qquad (Eq. 21)$$

where $z_{in}$ is the component along a second axis Z of the spatial position vector $r_{in}$ of the input virtual transducer $TV_{in}$, and determining a corrected focused reflection matrix $RFoc^{(1)}(r_{in}, r_{out}, \delta t)$ which comprises responses of the medium between an input virtual transducer $TV_{in}$ of spatial position $r_{in}$ and an output virtual transducer $TV_{out}$ of spatial position $r_{out}$, the responses each being obtained with a corrected speed of sound that is dependent on the input virtual transducer.

For each of these variants, the corrected focused reflection matrix $RFoc^{(1)}(r_{in}, r_{out}, \delta t)$ is an axial correction of the focused reflection matrix, i.e. a focused reflection matrix for which the axial aberrations have been corrected. Due to this corrected focused reflection matrix, it advantageously becomes possible to construct an ultrasound image with reduced axial aberrations. Thus, the distances in the axial direction in this corrected ultrasound image are more precise and make it possible, for example, to obtain images of better quality.

The corrected focused reflection matrix $RFoc^{(1)}(r_{in}, r_{out}, \delta t)$ is obtained by spatial translation, which is either a translation of the spatial position in the Z direction of the axial component of one or both virtual transducers ($TV_{in}$ and/or $TV_{out}$), or a translation by changing the speed of sound c. These alternatives make it possible to improve the beamforming step which is similar to a process of converting temporal information given by the experimental signals of the experimental reflection matrix $R_{ui}(t)$ (also often referred to as RF signals) into spatial information via the relation $t=z/c$. Thus, the spatial positions of the points of the medium are corrected axially in the depthwise direction Z, which makes it possible to obtain images with more precise vertical positioning.

Figure 12:
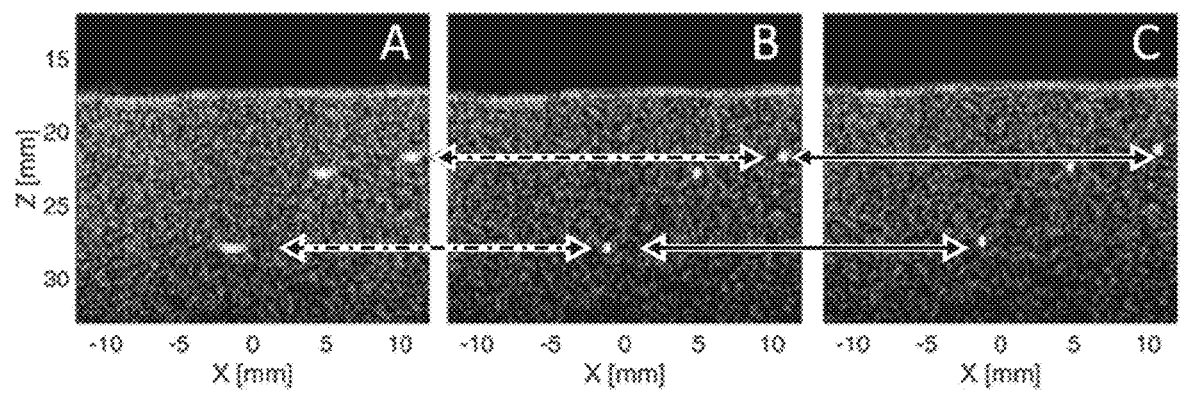
FIG. 12 shows ultrasound images obtained without aberration correction (image A), with the usual lateral aberration correction (image B), and with axial aberration correction using measurements in wavefront images according to this disclosure.

For example, FIG. 12 illustrates this process. In this FIG. 12, the image denoted A corresponds to an ultrasound image obtained with a speed of sound $c_0$ of $c_0$=1540 m/s which is the speed of sound in the phantom, but not that in the layer of water above the phantom which has a speed of sound of $c_{water}$=1480 m/s=1480 m/s. An ultrasound image A is therefore usually obtained with a degraded resolution and contrast due to the heterogeneity of the media studied. Known aberration correction techniques make it possible to obtain the image denoted B which is laterally improved and which gives an image of better quality than conventional techniques. However, in this image the depthwise positions of the reflective elements are not corrected (see the horizontal arrows between images A and B).

The image denoted C corresponds to an ultrasound image obtained by the axial correction proposed in the method presented above. In this image C, the reflective elements are shifted slightly upwards (towards the outer surface), which shows the influence of the reduced speed of sound in water compared to that of the phantom. Thus, due to this axial correction, the (depthwise) axial positions of the points of the image are closer to the true nature of the observed medium and the distances measured in such an image are closer to the exact values.

It is also possible to improve the technique of either of the above three variants, by determining improved wavefront images by using combinations of a set of wavefront images and determining the speed of sound both at input and at output as explained above in the part concerning the determination of the integrated speed of sound, and for example by a technique of singular value decomposition.

The plurality of wavefront images of the set are processed here by singular value decomposition in order to combine several acoustic disorder measurements or experiments in a region close to an input virtual transducer, which very advantageously makes it possible to improve the contrast of the wavefront image as well as its use.

Corrected Ultrasound Image with Correction of Axial Aberrations

The method for ultrasonic characterization in order to determine an axial correction and implemented by the calculation unit 42 of the system 40 can then be supplemented by constructing one or more corrected ultrasound images, a corrected ultrasound image being determined by calculating an ultrasound intensity value for a plurality of points of the medium each corresponding to an input virtual transducer $TV_{in}$ of spatial position $r_{in}$ based on the corrected focused reflection matrix $RFoc^{(1)}(r_{in}, r_{out}, \delta t)$ and by imposing an output virtual transducer $TV_{out}$ coincident with the input virtual transducer $TV_{in}$, i.e. $r_{in}=r_{out}$.

Determination of a Preferred Direction of Anisotropy of Scatterers in the Medium The method and system for ultrasonic characterization of a medium according to this disclosure and implemented by the calculation unit 42 of the system 40 is also able to locally determine a preferred direction of anisotropy of the scatterers in the medium.

Scatterer anisotropy characterizes any scatterer that is capable of generating echoes in a preferred direction when it is insonified in a particular incident direction. This anisotropy therefore concerns any scatterer whose dimensions are greater than the wavelength. In particular, this is of interest in cases of medical imaging of fibers, organ walls, surgical instruments such as biopsy needles, etc.

In this case, the method comprises steps similar or identical to those already explained above, up to:

determining a wavefront image for an input virtual transducer $TV_{in}$ and for an additional delay interval, said wavefront image being determined as described above as a function of a speed of sound $c_0$ in the medium.

The method further comprises:

determining a preferred direction of the focal spot in the wavefront image, by image processing said wavefront image.

Figure 13:
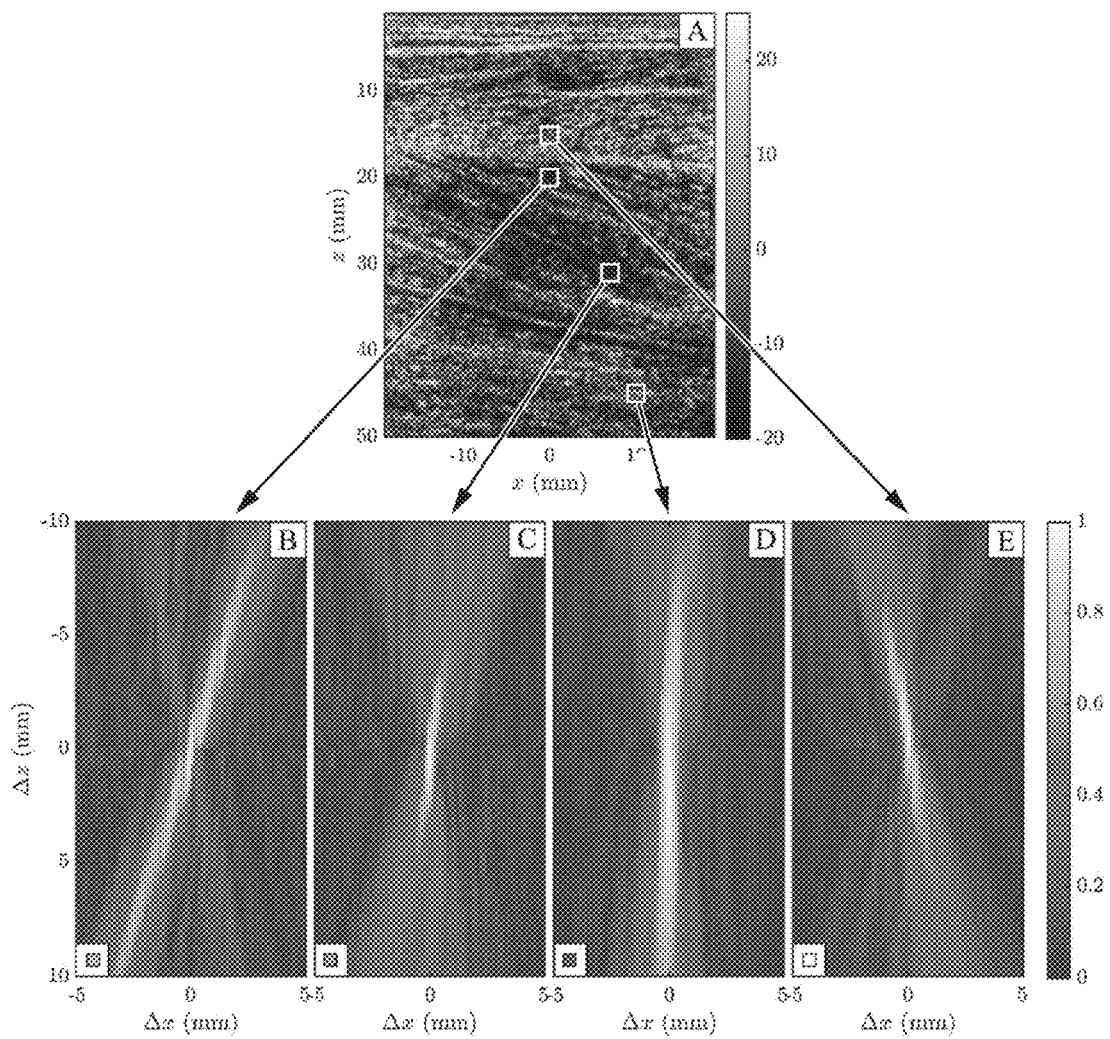
FIG. 13 shows an ultrasound image (A) comprising several areas with muscle fibers angled in various directions, and wavefront images (B, C, D, E) corresponding to these various areas of the medium.

For example, FIG. 13 illustrates this process. In this FIG. 13, the image denoted A corresponds to an ultrasound image with spatial variation in the direction of anisotropy of the tissues. The medium imaged in this ultrasound corresponds to a patient's muscle (a calf in this example) in which several regions are observed with fibers angled in very different directions. This application to an image of a muscle is only one example of an anisotropic medium to which the method can be applied. However, such a conventional ultrasound image gives distorted general information. Prior art ultrasound does not allow reliable observation of this anisotropy which is a local characteristic of the medium, because the propagation of ultrasonic waves in such a medium is neither at constant speed nor propagating in rectilinear directions from the transducers of the probe.

The images denoted B, C, D, and E of this FIG. 13 correspond to the images of the wavefront constructed for the small regions of the ultrasound image that are connected by the arrows. Here, these wavefront images are processed by singular value decomposition of a plurality of virtual transducers in each of these regions, in order to capture or probe a plurality of acoustic disorder experiments in this region and thus to improve the contrast of the wavefront image produced as well as its analysis.

All these wavefront images B, C, D, and E show a focal spot that is elongated in the vertical direction (direction of the depth axis $\Delta z$), but with a different inclination. This inclination of the focal spot in the wavefront image is local inclination information which is highly correlated with the actual value of the inclination of muscle fibers in the region considered. The axis of inclination of the focal spot is in fact substantially perpendicular to the direction of the fibers, in particular at the center of the image, locations where the incident wave has a direction substantially in the depthwise direction Z.

Thus, the method determines the preferred direction of the focal spot in the wavefront image by image processing this wavefront image.

According to a first variant, the method can for example extract an outline of the focal spot by a threshold at a level lower than the maximum value in this wavefront image, for example at 50% or 70% of this maximum. From this outline, we can deduce the preferred direction or main direction (the direction of greatest dimension for the focal spot), and the secondary direction (the direction of smallest dimension). However, other image processing techniques are possible to extract the preferred direction of the focal spot.

According to a second variant, the method may for example:

convert the wavefront image $U(r_{in}, \Delta x_{out}, \Delta z_{out})$ from a reference system in Cartesian coordinates to a reference system in polar coordinates, of the type $U(r_{in}, \Delta s_{out}, \Delta \phi_{out})$ sum the values of said wavefront image that is in the reference system in polar coordinates, over a plurality of radial distance deviation values $\Delta s_{out}$, to obtain an angular sensitivity function $f(r_{in}, \Delta \phi_{out})$ for a plurality of angular values $\Delta \phi_{out}$, determine the optimum angular value $\Delta \phi^{max}_{out}(r_{in})$ corresponding to the maximum of the angular sensitivity function, said optimum angular value $\Delta \phi^{max}_{out}(r_{in})$ corresponding to the preferred direction of the focal spot associated with the input virtual transducer $TV_{in}$.

We thus have:

$$\Delta \phi^{max}_{out}(r_{in}) = \max_{\Delta \phi_{out}} \left[ \sum_{\Delta s_{in}} U(r_{in}, \Delta s_{out}, \Delta \phi_{out}) \right] \quad \text{(Eq. 22)}$$

Figure 14:
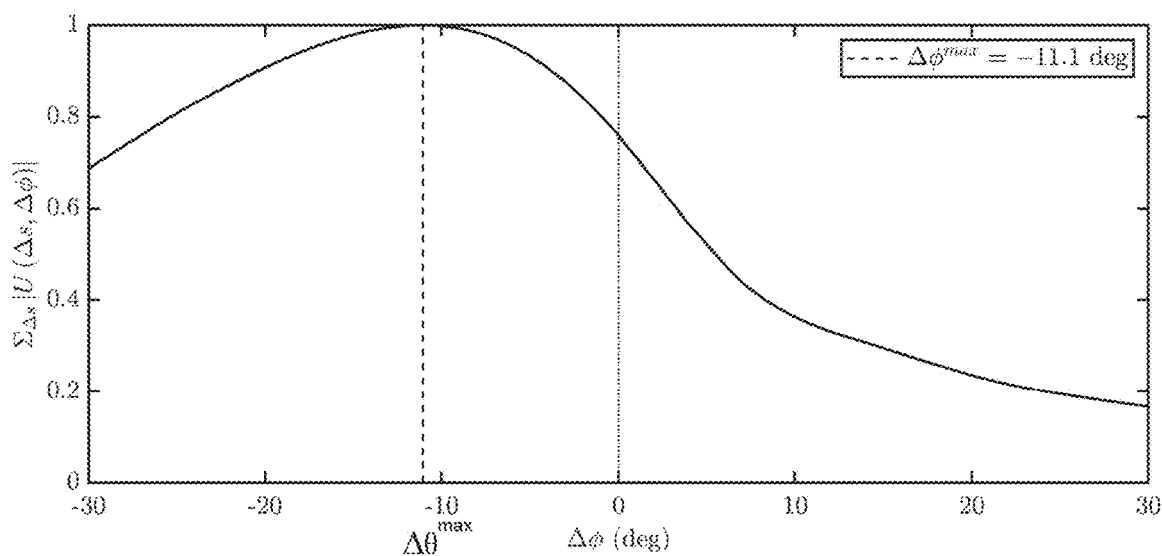
FIG. 14 shows a curve for calculating the angle of a preferred direction of inclination of muscle fiber in the medium.

FIG. 14 shows an example curve of an angular sensitivity function $f(r_{in}, \Delta \phi_{out})$ for said wavefront image using the reference system in polar coordinates corresponding to FIG. 13B, said angular sensitivity function in this illustrative example being normalized to have a maximum value equal to one (1). This curve has a maximum towards $\Delta \phi_{out} = -11°$ which is the estimated angle of the local preferred direction at the point concerned in the medium of this example.

Optionally, a correction is applied to the angular value $\Delta \phi_{out}$, corresponding to the angle of view of the point concerned in the medium as viewed from the transducers, in order to obtain an angular anisotropy value $\gamma_{out}(r_{in})$, which is characteristic of the direction of anisotropy of the scatterers located at the spatial position of the input virtual transducer.

Here, this estimation is made based on correlation of the output signals. Conversely, one can estimate another angular anisotropy value $\gamma_{in}(r_{out})$, which is characteristic of the direction of anisotropy of the scatterers located at the spatial position of the output virtual transducer. Advantageously, it is possible to combine the two angular anisotropy values $\gamma_{out}(r_{in})$ and $\gamma_{in}(r_{out})$, to obtain a better local characterization of the direction of anisotropy of the medium.

According to one example, the method could be supplemented by the following operations:

of input virtual transducer(s) and the output virtual transducer(s) are reversed in order to determine a preferred direction relative to an output virtual transducer, and the preferred direction with reference to the input virtual transducer and the preferred direction with reference to the output virtual transducer are combined to obtain an improved preferred direction.

According to another example, the method could be supplemented by the following operations:

the roles of the input virtual transducer(s) and of the output virtual transducer(s) are reversed in order to determine an angular anisotropy value relative to an output virtual transducer $\gamma_{out}(r_{out})$, and the angular anisotropy value with reference to the input virtual transducer $\gamma_{out}(r_{in})$ and the angular anisotropy value with reference to the output virtual transducer $\gamma_{out}(r_{out})$ are combined to obtain an improved angular anisotropy value.

An example calculation of an angular anisotropy value can be given by the following formula (in the first case an angular anisotropy value with reference to the input virtual transducer $\gamma_{out}(r_{in})$):

$$\gamma_{out}(r_{in}) = -2(\Delta \phi^{max}_{out}(r_{in}) - \hat{\theta}_{out}(r_{in})) \quad \text{(Eq. 23)}$$

Such a calculation of the angular anisotropy value comes for example from calculations explained in the document "*Specular Beamforming*", Alfonso Rodriguez-Molares et al., published in *IEEE Transactions on Ultrasonics, Ferroelectrics, and Frequency Control* (Volume: 64, Issue: 9, September 2017).

We add a definition of a viewing angle of the point of spatial position $r_{in}$ of the input virtual transducer, for example of the type:

$$\hat{\theta}_{out}(r_{in}) = \frac{1}{\sum_{u_{out}^-}^{u_{out}^+} \cos(\theta_{out}(r_{in}))} \sum_{u_{out}^-}^{u_{out}^+} \theta_{out}(r_{in}) \cos(\theta_{out}(r_{in})) \quad \text{(Eq. 24)}$$

with $$\theta_{out}(r_{in}) = a\tan\left(\frac{u_{out} - x_{in}}{z_{in}}\right)$$

where:

$u_{out}^{\pm}(r)$ are the maximum and minimum values of the spatial positions of transducers of the array.

Other formulas for calculating the angular anisotropy value are conceivable for the technician skilled in the art, in order to obtain more realistic values for the angle of preferred direction.

Figure 15:
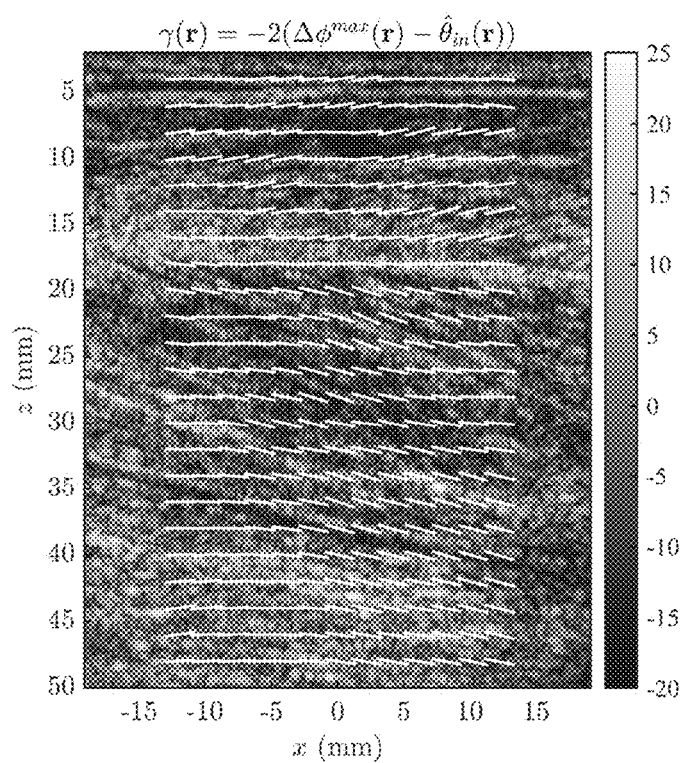
FIG. 15 shows a matrix of determined preferred directions superimposed on an ultrasound image of a medium with muscle fibers.

FIG. 15 shows an ultrasound image on which are superimposed lines corresponding to estimations of preferred directions for a set of points distributed over the ultrasound image. One will note the great consistency between the estimated preferred directions and the underlying structures visible in the ultrasound image. The proposed method advantageously makes it possible to adequately estimate the preferred directions over the entire ultrasound image.

The measurement of this preferred direction, the angle of inclination of the focal spot for its largest dimension, is an important parameter for improving the quality of the ultrasound image in this region: knowing this can make it possible to adapt the characteristics of the incident ultrasonic waves $US_{in}$, for example by choosing plane waves with a specific inclination or waves focused in a specific place. This also makes it possible to adapt the apodizations chosen at reception during the beamforming step.

The measurement of this local preferred direction can make it possible to analyze the degree of anisotropy of a larger region, thereby determining the potential existence of lesions in the tissue and finding their location.

Thus, the method for ultrasonic characterization of a medium in order to locally determine a preferred direction of anisotropy, comprises the following operations:

generating a series of incident ultrasonic waves $US_{in}$ in an area of said medium, by means of an array 10 of transducers 11, said series of incident ultrasonic waves being an emission basis i; and generating an experimental reflection matrix $R_{ui}(t)$ defined between the emission basis i as input and a reception basis u as output;

determining a focused reflection matrix $RFoc(r_{in}, r_{out}, \delta t)$ which comprises responses of the medium between an input virtual transducer $TV_{in}$ of spatial position $r_{in}$ and an output virtual transducer $TV_{out}$ of spatial position $r_{out}$, the responses of the output virtual transducer $TV_{out}$ being obtained at a time instant that is shifted by an additional delay $\delta t$ relative to a time instant of the responses of the input virtual transducer $TV_{in}$, determining a wavefront image for the input virtual transducer $TV_{in}$ and for an additional delay interval, said wavefront image being determined as a function of the speed of sound $c_0$ in the medium, and said wavefront image being determined based on:

the focused reflection matrix $RFoc(r_{in}, r_{out}, \delta t)$ and
a ballistic propagation relation of the type $\delta t(\Delta r_{out}) = -\text{sign}(\Delta z_{out}) \cdot |\Delta r_{out}|c_0$, which allows extracting values from the focused reflection matrix to construct the wavefront image, and where:

$\delta t$ is the additional delay, $\Delta r_{out}$ is the modulus of the vector between the input virtual transducer $TV_{in}$ and the output virtual transducer $TV_{out}$, with $\Delta r_{out} = r_{out} - r_{in}$, $\Delta z_{out}$ is the component along a depth axis Z of the spatial position vector $\Delta r_{out}$, and determining a preferred direction of the focal spot in the wavefront image by image processing said wavefront image.

It is possible to improve the proposed technique by determining improved wavefront images using combinations of a set of wavefront images as explained above in the part concerning determination of the integrated speed of sound, and for example by a singular value decomposition technique. In this case, the preferred direction obtained from an improved wavefront image makes it possible to characterize the anisotropy of the medium corresponding to a chosen coherence area and is attributed to the spatial position $r_{in,ref}$ of the reference virtual transducer.

Here, the plurality of wavefront images of the set are processed by singular value decomposition in order to combine several acoustic disorder measurements or experiments in a region close to an input virtual transducer, which makes it possible to improve the contrast of the wavefront image, and thus its use.

In the method, the following operations can thus be added:

between determining a wavefront image and determining the preferred direction of the focal spot, improving the wavefront image is performed in which a linear combination of a set of wavefront images corresponding to a coherence area is carried out, each wavefront image being obtained between a selected input virtual transducer ($TV_{in}$) of different spatial position $r_{in}$, and output virtual transducers ($TV_{out}$) of spatial position $r_{out}$ such that $r_{out} = \Delta r_{out} + r_{in}$, with $\Delta r_{out}$ being predefined and identical for all wavefront images of the set, and the selected input virtual transducers being close to each other, in order to obtain an improved wavefront image associated with a reference input virtual transducer ($TV_{in,ref}$), this reference input virtual transducer $TV_{in,ref}$ being characteristic of the input virtual transducers of the set of wavefront images used and associated with the coherence area ZC, and in determining a preferred direction of the focal spot, the improved wavefront image is used instead of the wavefront image; the preferred direction of the focal spot is relative to the spatial position of the reference input virtual transducer $TV_{in,ref}$.

In addition, by reversing the role of the input $TV_{in}$ and output $TV_{out}$ virtual transducers, in other words by reversing the "in" and "out" notations, it is possible to determine the preferred direction $\Delta\phi^{max}_{in}(r_{out})$ of the focal spot associated with the output virtual transducer $TV_{out}$ of spatial position $r_{out}$. Combining the two preferred directions associated with position r, i.e. $\Delta\phi^{max}_{in}(r)$ and $\Delta\phi^{max}_{out}(r)$, makes it possible to improve the measurement of scatterer anisotropy.

Due to this calculation of the preferred direction and of these images, we can characterize the anisotropy of the scatterers of the medium, or characterize for example an anisotropic structure in the medium, such as a needle introduced into tissue, or a wall separating different tissues. Anisotropy of scatterers is understood to mean any element greater than the wavelength of the ultrasonic waves.

Analysis of Time Signals for Confocal Points

The method and system for ultrasonic characterization of a medium according to this disclosure and implemented by the calculation unit 42 of the system 40 is also able to perform a local spectral analysis of an ultrasonic focusing.

In such an analysis, confocal responses are of particular interest, meaning an input virtual transducer $TV_{in}$ of spatial position $r_{in}$ superimposed on the output virtual transducer $TV_{out}$ of spatial position $r_{out}$; i.e. with $r_{in}=r_{out}=r$.

The additional delay $\delta t$ is then used to probe the time response of the scatterers selected by these virtual transducers.

In this case, the method comprises the following operations, already explained, to obtain a focused reflection matrix, but applied to a same spatial position, i.e. a confocal position:

generating a series of incident ultrasonic waves $US_{in}$ in an area of said medium, by means of an array 10 of transducers 11, said series of incident ultrasonic waves being an emission basis i; and generating an experimental reflection matrix $R_{ui}(t)$ defined between the emission basis i as input and a reception basis u as output; and determining a focused reflection matrix $RFoc(r, \delta t)$ which comprises responses of the medium between an input virtual transducer $TV_{in}$ of spatial position $r_{in}$ and an output virtual transducer $TV_{out}$ of spatial position $r_{out}$, the input and output virtual transducers being superimposed at the same spatial position r, with $r_{in}=r_{out}=r$, and the responses of the output virtual transducer $TV_{out}$ being obtained at a time instant that is shifted by an additional delay $\delta t$ relative to a time instant of the responses of the input virtual transducer $TV_{in}$.

The method then comprises the following operations which make it possible to perform the local spectral analysis:

determining a frequency matrix $RFreq_t(r, \omega)$ which is a temporal Fourier transform of the focused reflection matrix $RFoc(r, \delta t)$ $$RFreq_t(r,\omega)=TF_t[RFoc(r,\delta t)] \qquad \text{(Eq. 25)}$$

where $TF_t$ is the temporal Fourier transform, and $\omega$ is a pulse with $\omega=2\pi f$, f being the frequency corresponding to said pulse.

The temporal Fourier transform can be explained for example by the following discrete-time Fourier transform formula:

$$RFreq_t(r, \omega) = TF_t[RFoc(r, \delta t)] = \sum_{\Delta\omega} RFoc(r, \delta t) e^{-i\omega \delta t} \qquad \text{(Eq. 26)}$$

Other Fourier transform and temporal Fourier transform formulations exist, for example in discrete or continuous form, with or without normalization, and can also be used.

$RFreq_t(r, \omega)$ then contains a local estimate of the spectrum of the echoes backscattered by the medium. More precisely, these echoes come from scatterers which are comprised in the monochromatic focal spot centered on position r. In the absence of an aberration, these dimensions are therefore provided for by the diffraction limits defined at the central frequency of the echoes backscattered by the medium.

This method can therefore be supplemented by any medical imaging technique based on frequency analysis of the backscattered echoes for the purpose of improving the spatial resolution. Specifically, this method allows spatial beamforming at reception for each frequency, before performing any spectral analysis. It should be noted that a confocal configuration advantageously makes it possible to limit pulse diffraction phenomena.

For example, this method can be supplemented by a filtering operation during which a frequency filtering of elements of the frequency matrix $RFreq_t(r, \omega)$ is carried out. In particular, it is possible to perform low-pass, band-pass, or high-pass frequency filtering, in order to extract the desired components in the responses of the focused reflection matrix, according to the target application. For example, the frequency filtering can optionally be adapted to extract harmonic components of a fundamental frequency of the incident ultrasonic waves $US_{in}$.

Figure 16:
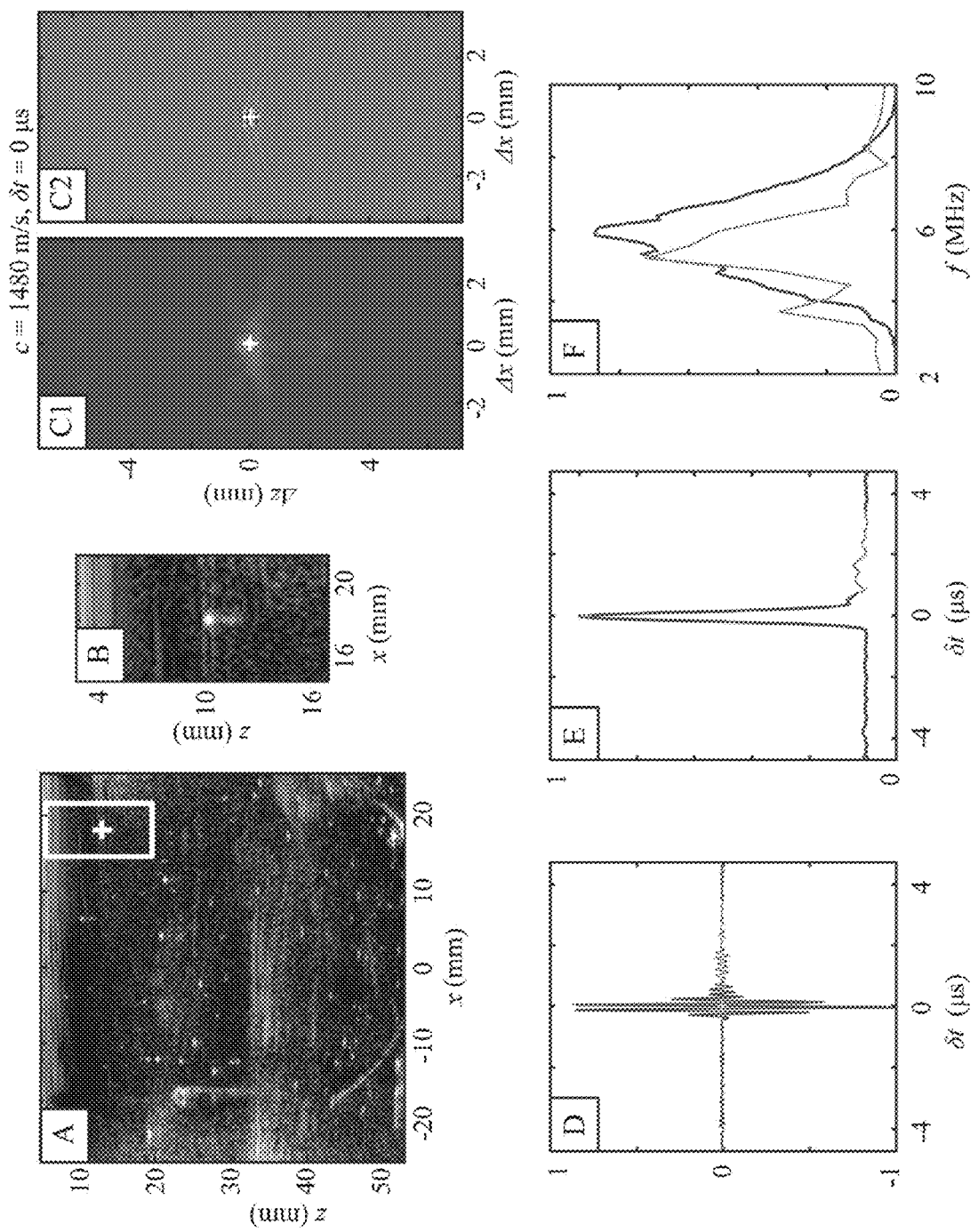
FIG. 16 shows an ultrasound image (A), an enlargement of an area of this ultrasound image (B) around a particular point, the real part of the local time signal (C) and the estimated amplitude (D) for this particular point, and the spectral analysis of this local time signal of the medium.

For example, FIG. 16 illustrates this process. In this FIG. 16, the image denoted A illustrates an ultrasound image of a medium comprising bubbles. These bubbles are resonant structures in the medium which disrupt the ultrasonic image, because they continue to oscillate after the passage of an incident wave. They thus generate echoes which reach the receiving transducers with a time-of-flight greater than the ballistic time-of-flight, which produces artifacts in the ultrasound image downstream of the bubble. The image denoted B in FIG. 14 shows an enlargement of image A in which a bright echo of a bubble is observed at spatial position r=[x, z]=[11, 17] mm, and its downstream artifact located below this position (i.e. vertically depthwise) The images denoted C1 and C2 respectively correspond to the amplitude and the real part for the propagation image, for an additional delay $\delta t$ of zero.

The focused reflection matrix $RFoc(r, \delta t)$ of the method makes it possible to study the time signals of this bubble's oscillation. The images denoted D-E-F in FIG. 14 respectively correspond to the plots of the real part, the amplitude, and the frequency spectrum of the response $RFoc(r, \delta t)$ at the point of spatial position r corresponding to the position of this bubble. On images D and E, a second echo is observed at about 1.5 µs after the main echo centered at $\delta t=0$. Image F shows a first spectrum plot excluding this second echo and a second spectrum plot with this second echo. This second spectrum plot comprises a main frequency around 6 MHz which corresponds to the frequency of the incident wave, and another frequency around 3 MHz which corresponds to the resonant frequency (oscillation) of the bubble.

The method thus performs a spectral analysis which makes it possible, for example, to identify the resonant frequencies of bubbles or of any other resonant structure in the observed medium.

It is thus possible to filter, for example by a predetermined band-pass filter, the responses of the focused reflection matrix, and then to calculate an improved ultrasound image using these filtered responses. The effect of the resonances can then be attenuated or eliminated in the ultrasound image.

Conversely, it is possible to construct resonant frequency images by keeping only those resonances in the responses of the focused reflection matrix. Note that the resonant frequency of a bubble is linked to its size, and can be used to estimate a local pressure in the medium.

In a second example, $RFreq_t(r, \omega)$ can be used to study the attenuation of the medium. Indeed, this phenomenon depends on the frequency. Since high frequencies are more attenuated than low frequencies, it is possible to deduce an attenuation coefficient, for example by comparing the spectrum of echoes coming from two different depths in the observed medium. The technique described above for estimating the local spectrum of echoes from a given area is therefore ideal for determining attenuation. To do so, the method can for example be supplemented with determining an average spectrum at depth S(z, ω), determined by an average of the spectra of the frequency matrix at a predetermined depth z in the medium.

For example, this average spectrum at a depth is calculated by the following formula, which is a normalized average, averaged over a set of spatial positions of the same depth z and of lateral coordinate x comprised within a predetermined interval.

$$S(z, \omega) = \left\langle \frac{RFreq_t(r, \omega)}{\max_{\omega}[RFreq_t(r, \omega)]} \right\rangle_x \qquad \text{(Eq. 27)}$$

Figure 17:
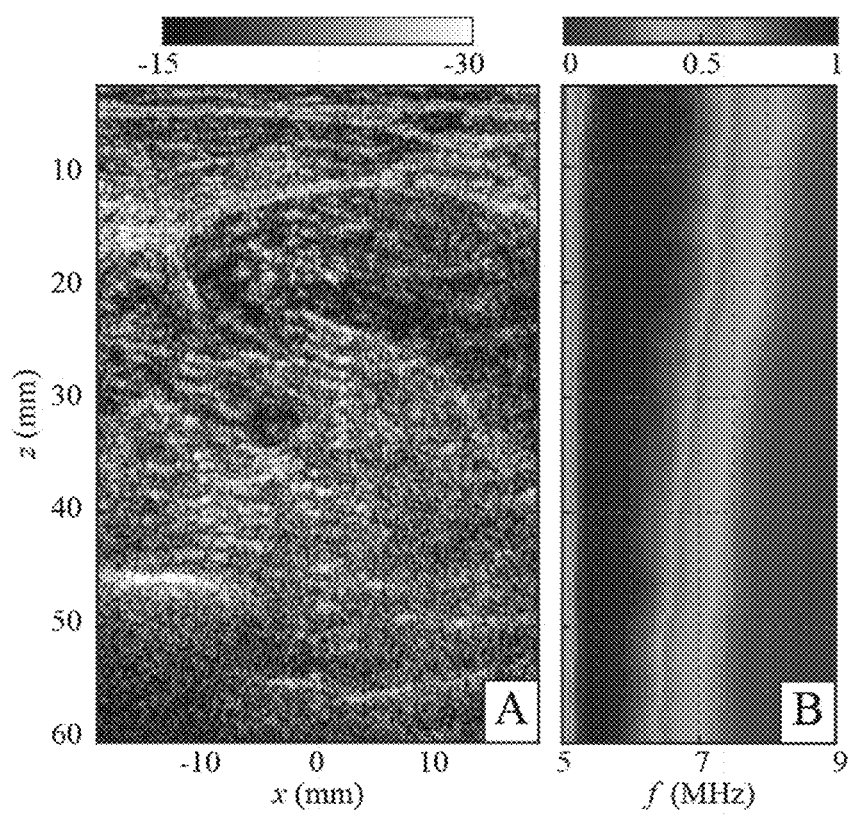
FIG. 17 shows an ultrasound image (A) and an estimate of the average spectrum as a function of the depth Z for the corresponding ultrasound image of this figure.

For example, FIG. 17 illustrates this calculation of the average spectrum depth wise, by constructing an image of the set of spectra for all depths of an ultrasound image. In this FIG. 17, the image denoted A illustrates an in-vivo ultrasound image of the calf of a healthy individual and the image denoted B shows the average spectra depthwise in grayscale. This image of depthwise spectra shows the strongest attenuation of high frequencies for large depths.

Using such an image, we can estimate the evolution of the attenuation as a function of the depth by using the entire frequency content, via techniques for adjusting between a theoretical and/or experimental model, and such an image.

In a third example, the method can also be supplemented with determining the spectral correlation width δω(r) for the point of spatial position r, by calculating the full width at half maximum of the autocorrelation of each spectrum of the frequency matrix RFreq$_t$(r, ω), i.e. by the following formula:

$$\delta\omega(r) = FWHM(\frac{1}{\Delta\omega} \int_{\omega^-}^{\omega^+} RFreq_t(r, \omega)RFreq_t^*(r, \omega + d\omega)d\omega \qquad \text{(Eq. 28)}$$

where

FWHM is the function for calculating the full width at half maximum ( )* is the complex conjugate function, ω$^-$ and ω$^+$ are the bounding pulses, Δω=ω$^+$−ω$^-$ is the interval between the bounding pulses, i.e. the ultrasonic wave bandwidth concerned.

Due to the spatial resolution of the matrix RFreq$_t$(r, ω), the spectral correlation width δω(r) is a local value which can be used to characterize the nature of the scatterers contained in the monochromatic focal spot centered on spatial position r. If the focal spot contains a single non-resonant scatterer, the spectral correlation width δω(r) is of the order of magnitude of the bandwidth of the ultrasonic signal. If the focal spot contains a set of randomly distributed scatterers of the same intensity (ultrasonic speckle conditions), the value of the spectral correlation width δω(r) becomes much smaller than the bandwidth Δω.

The method can also comprise a step of determining at least one spectral correlation image, said spectral correlation image being obtained by determining the spectral widths δω(r) for a plurality of points of the medium each corresponding to a point of the medium of spatial position r.

Figure 18:
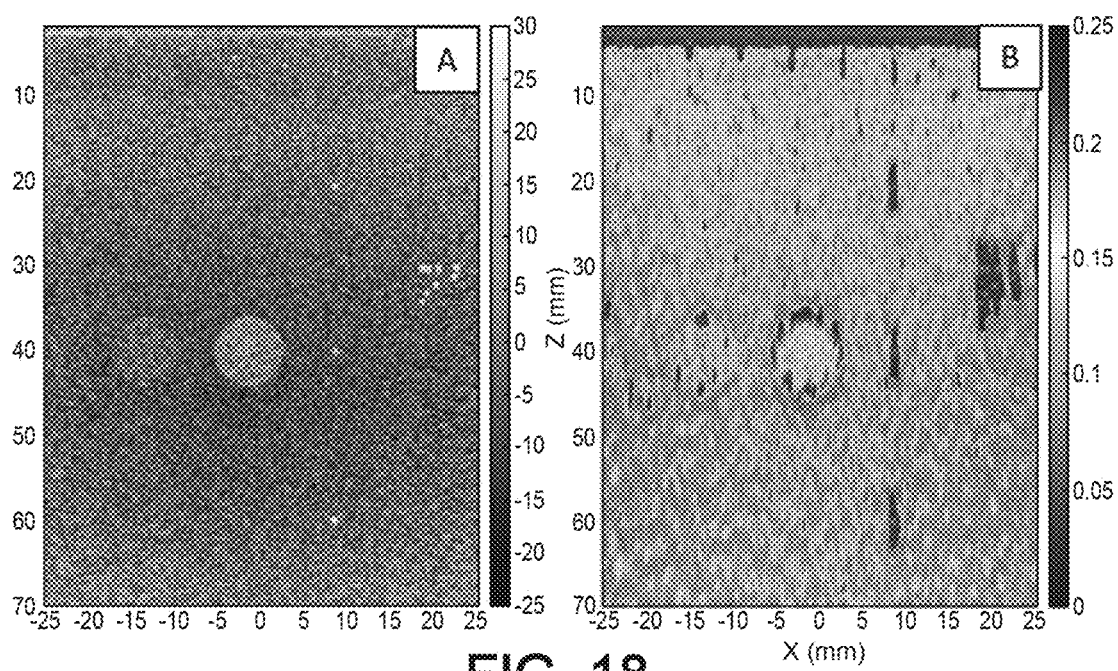
FIG. 18 shows an ultrasound image (A) and the spectral correlation image determined for the corresponding ultrasound image of this figure.

For example, FIG. 18 illustrates this process. In this FIG. 18, the image denoted A is an ultrasound image of a phantom medium containing several different elements: point targets and an echogenic cylinder. The corresponding image denoted B is the spectral correlation image of the previous ultrasound image, obtained by calculating the spectral correlation width δω(r) for a set of points of this medium. In this image B, the edges of the cylinder and the point targets have a spectral correlation width δω(r) that is greater than the rest of the medium which is composed of a large number of randomly distributed sub-resolution scatterers.

By means of this calculation of the spectral correlation width and of these images, it is possible to characterize the nature of the targets in the medium. For example, it is possible to differentiate between a bright speckle spot and a single scatterer. For example, this can help identify bubbles for contrast imaging, or micro-calcifications characteristic of the presence of tumors, especially in breast cancer.

The invention claimed is:

1. Method for ultrasonic characterization of a medium in order to locally determine a preferred direction of anisotropy of scatterers in the medium, the method comprising:
   generating a series of incident ultrasonic waves (US$_{in}$) in an area of said medium, by means of an array of transducers, said series of incident ultrasonic waves being an emission basis (i);
   generating an experimental reflection matrix R$_{ui}$(t) defined between the emission basis (i) as input and a reception basis (u) as output;
   determining a focused reflection matrix RFoc(r$_{in}$, r$_{out}$, δt) which comprises responses of the medium between an input virtual transducer (TV$_{in}$) of spatial position rill and an output virtual transducer (TV$_{out}$) of spatial position r$_{out}$, the responses of the output virtual transducer (TV$_{out}$) being obtained at a time instant that is shifted by an additional delay δt relative to a time instant of the responses of the input virtual transducer (TV$_{in}$),
   determining a wavefront image for the input virtual transducer (TV$_{in}$) and for an additional delay interval, said wavefront image being determined as a function of the speed of sound co in the medium, and said wavefront image being determined based on:
      the focused reflection matrix RFoc(r$_{in}$, r$_{out}$, δt) and
      a ballistic propagation relation of the type δt(Δr$_{out}$)=−sign(Δz$_{out}$)·|Δr$_{out}$|/c$_0$, which makes it possible to extract values from the focused reflection matrix in order to construct the wavefront image, and where:
   δt is the additional delay,
   |Δr$_{out}$| is the modulus of the vector between the input virtual transducer (TV$_{in}$) and the output virtual transducer (TV$_{out}$), with Δr$_{out}$=r$_{out}$−r$_{in}$,
   Δz$_{out}$ is the component along a depth axis Z of the spatial position vector Δr$_{out}$; and
      determining a preferred direction of the focal spot in the wavefront image by image processing said wavefront image.

2. Method according to claim 1, wherein the image processing comprises extracting the outline of the focal spot by a threshold at a level lower than the maximum value in the wavefront image, this outline serving to determine the preferred direction of the focal spot.

3. Method according to claim 1, wherein:
   the wavefront image U(r$_{in}$, Δx$_{out}$, Δz$_{out}$) is converted from a reference system in Cartesian coordinates to a reference system in polar coordinates U(r$_{in}$, Δs$_{out}$, Δϕ$_{out}$),
   the values of said wavefront image in the reference system in polar coordinates are summed, over a plurality of radial distance deviation values Δs$_{out}$, to obtain an angular sensitivity function $f(r_{in}, \Delta\phi_{out})$ for a plurality of angular values $\Delta\phi_{out}$, the optimum angular value $\Delta\phi^{max}_{out}(r_{in})$ corresponding to the maximum of the angular sensitivity function is determined, said optimum angular value $\Delta\phi^{max}_{out}(r_{in})$ corresponding to the preferred direction of the focal spot associated with the input virtual transducer ($TV_{in}$).

4. Method according to claim 1, wherein the preferred direction is corrected by an angle of view of the point of spatial position $r_{in}$ of the input virtual transducer ($TV_{in}$) as viewed from the array of transducers.

5. Method according to claim 4, wherein the preferred direction is corrected by the formula:

$$\gamma_{out}(r_{in}) = -2(\Delta\phi_{out}^{max}(r_{in}) - \hat{\theta}_{out}(r_{in}))$$

where:

$\Delta\phi_{out}^{max}(r_{in})$ is the value of the preferred direction,
$\hat{\theta}_{out}(r_{in})$ is the correction of the angle of view,
$\gamma_{out}(r_{in})$ is the angular anisotropy value.

6. Method according to claim 5, wherein the correction of the angle of view is:

$$\hat{\theta}_{out}(r_{in}) = \frac{1}{\sum_{u_{out}^-}^{u_{out}^+} \cos(\theta_{out}(r_{in}))} \sum_{u_{out}^-}^{u_{out}^+} \theta_{out}(r_{in})\cos(\theta_{out}(r_{in}))$$

with $$\theta_{out}(r_{in}) = a\tan\left(\frac{u_{out} - x_{in}}{z_{in}}\right)$$

where:

$u_{out}^{\pm}(r)$ are the maximum and minimum values of positions of transducers in the array.

7. Method according to claim 1, wherein:

the roles of the input virtual transducer(s) and of the output virtual transducer(s) are reversed in order to determine a preferred direction with respect to an output virtual transducer, and the preferred direction with reference to the input virtual transducer and the preferred direction with reference to the output virtual transducer are combined to obtain an improved preferred direction.

8. Method according to claim 5, wherein:

the roles of the input virtual transducer(s) and of the output virtual transducer(s) are reversed in order to determine an angular anisotropy value with respect to an output virtual transducer $\gamma_{out}(r_{out})$, and the angular anisotropy value with reference to the input virtual transducer $\gamma_{out}(r_{in})$ and the angular anisotropy value with reference to the output virtual transducer $\gamma_{out}(r_{out})$ are combined to obtain an improved angular anisotropy value.

9. Method according to claim 1, wherein:

between determining a wavefront image and determining the preferred direction of the focal spot, improving the wavefront image is performed in which a linear combination of a set of wavefront images corresponding to a coherence area is carried out, each wavefront image being obtained between a selected input virtual transducer ($TV_{in}$) of a different spatial position $r_{in}$, and output virtual transducers ($TV_{out}$) of spatial position $r_{out}$ such that $r_{out} = \Delta r_{out} + r_{in}$, with $\Delta r_{out}$ being predefined and identical for all wavefront images of the set, and the selected input virtual transducers being close to each other, in order to obtain an improved wavefront image associated with a reference input virtual transducer ($TV_{in,ref}$), this reference input virtual transducer $TV_{in,ref}$ being characteristic of the input virtual transducers of the set of wavefront images used and associated with the chosen coherence area ZC, and in determining a preferred direction of the focal spot, the improved wavefront image is used instead of the wavefront image, the preferred direction of the focal spot is relative to the spatial position of the reference input virtual transducer $TV_{in,ref}$.

10. Method according to claim 9, wherein the linear combination is determined by calculating the singular value decomposition (SVD) of the set of wavefront images in order to obtain a singular vector ($W_1$) associated with the singular value of greatest absolute value of the singular value decomposition, this singular vector ($W_1$) then being the improved wavefront image corresponding to said reference input virtual transducer ($TV_{in,ref}$) and for the same additional delays $\delta t$.

11. Method according to claim 1, wherein, in determining the focused reflection matrix:

the calculation of the responses of the input virtual transducer ($TV_{in}$) corresponds to a focusing process at input based on the experimental reflection matrix $R_{ui}(t)$ which uses an outward time-of-flight of the waves between the emission basis and the input virtual transducer ($TV_{in}$) to create an input focal spot at spatial position $r_{in}$, the calculation of the responses of the output virtual transducer ($TV_{out}$) corresponds to a focusing process at output based on the experimental reflection matrix $R_{ui}(t)$ which uses a return time-of-flight of the waves between the output virtual transducer ($TV_{out}$) and the transducers of the reception basis u, to create an output focal spot at spatial position $r_{out}$, and the additional delay $\delta t$ being a time lag added to the outward and return times-of-flight during the focusing processes.

12. Method according to claim 1, wherein the focused reflection matrix is calculated by the following formula:

$$RFoc(r_{in}, r_{out}, \delta t) = \frac{1}{N_{in}N_{out}} \sum_{i_{in}} \sum_{u_{out}} R_{ui}(u_{out}, i_{in}, \tau(r_{in}, r_{out}, u_{out}, i_{in}, \delta t))$$

where $N_{in}$ is the number of elements of the emission basis (i),
$N_{out}$ is the number of elements of the reception basis (u) at output,
$R_{ui}(t)$ is the experimental reflection matrix, in which $R_{ui}(u_{out}, i_{in}, \tau(r_{in}, r_{out}, u_{out}, i_{in}, \delta t))$ is the element of the experimental reflection matrix $R_{ui}(t)$ recorded by the transducer of spatial position $u_{out}$ following the emission of index $i_{in}$ in the emission basis and at time $\tau$,
$\tau$ is a time which is the sum of the outward time-of-flight $\tau_{in}$ of the ultrasonic wave between the transducers of the emission basis (i) and the input virtual transducer ($TV_{in}$) of spatial position $r_{in}$, and of the return time-of-flight $\tau_{out}$ of the ultrasonic wave between the output transducer ($TV_{out}$) of spatial position $r_{out}$ and the transducers of the reception basis u, and of the additional delay $\delta t$, as explained by the following formula:

$$\tau(r_{in}, r_{out}, u_{out}, i_{in}, \delta t) = \tau_{in}(r_{in}, i_{in}) - \tau_{out}(r_{out}, u_{out}) + \delta t$$

13. System for ultrasonic characterization of a medium in order to locally determine a preferred direction of anisotropy of scatterers in the medium, the system comprising:

an array of transducers that are suitable for generating a series of incident ultrasonic waves in an area of the medium, and for recording the ultrasonic waves backscattered by said area as a function of time; and a calculation unit connected to the array of transducers and suitable for implementing the method according to one of the preceding claims.

14. System for ultrasonic characterization of a medium in order to determine a temporal and local characterization of an ultrasonic focusing, the system comprising:

an array of transducers that are suitable for generating a series of incident ultrasonic waves in an area of the medium, and for recording the ultrasonic waves backscattered by said area as a function of time;

one or more processors; and a memory storing instructions that, when executed by the one or more processors, cause the system to perform operations comprising:

generating a series of incident ultrasonic waves ($US_{in}$) in an area of said medium, by means of an array of transducers, said series of incident ultrasonic waves being an emission basis (i);

generating an experimental reflection matrix $R_{ui}(t)$ defined between the emission basis (i) as input and a reception basis (u) as output;

determining a focused reflection matrix $RFoc(r_{in}, r_{out}, \delta t)$ which comprises responses of the medium between an input virtual transducer ($TV_{in}$) of spatial position $r_{in}$ and an output virtual transducer ($TV_{out}$) of spatial position $r_{out}$, the responses of the output virtual transducer ($TV_{out}$) being obtained at a time instant that is shifted by an additional delay $\delta t$ relative to a time instant of the responses of the input virtual transducer ($TV_{in}$), determining a wavefront image for the input virtual transducer ($TV_{in}$) and for an additional delay interval, said wavefront image being determined as a function of the speed of sound $c_0$ in the medium, and said wavefront image being determined based on:

the focused reflection matrix $RFoc(r_{in}, r_{out}, \delta t)$ and a ballistic propagation relation of the type $\delta t(\Delta r_{out}) = -\text{sign}(\Delta z_{out}) \cdot |\Delta r_{out}|/c_0$, which makes it possible to extract values from the focused reflection matrix in order to construct the wavefront image, and where:

$\delta t$ is the additional delay, $|\Delta r_{out}|$ is the modulus of the vector between the input virtual transducer ($TV_{in}$) and the output virtual transducer ($TV_{out}$), with $\Delta r_{out} = r_{out} - r_{in}$, $\Delta z_{out}$ is the component along a depth axis Z of the spatial position vector $\Delta r_{out}$; and determining a preferred direction of the focal spot in the wavefront image by image processing said wavefront image.

* * * * *